(12) United States Patent
Hayakawa et al.

(10) Patent No.: US 7,815,632 B2
(45) Date of Patent: Oct. 19, 2010

(54) LASER INDUCED LIQUID JET GENERATING DEVICE

(75) Inventors: Koichi Hayakawa, Machida (JP); Kohei Watanabe, Hadano (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1239 days.

(21) Appl. No.: 11/391,225

(22) Filed: Mar. 29, 2006

(65) Prior Publication Data

US 2006/0247743 A1 Nov. 2, 2006

(30) Foreign Application Priority Data

Mar. 29, 2005 (JP) ............................. 2005-095138
Feb. 8, 2006 (JP) ............................. 2006-031214

(51) Int. Cl.
*A61B 17/00* (2006.01)
(52) U.S. Cl. ............................. 606/14; 606/15; 604/19
(58) Field of Classification Search ............... 606/2–19; 607/88–95
See application file for complete search history.

(56) References Cited

U.S. PATENT DOCUMENTS

| | | | |
|---|---|---|---|
| 4,690,672 A | 9/1987 | Veltrup et al. | |
| 5,203,781 A * | 4/1993 | Bonati et al. | 606/15 |
| 6,106,516 A * | 8/2000 | Massengill | 606/15 |
| 6,117,128 A * | 9/2000 | Gregory | 606/7 |

(Continued)

FOREIGN PATENT DOCUMENTS

DE 42 37 154 C1 3/1994

(Continued)

OTHER PUBLICATIONS

T.Hirano et al., "Fibrinolysis with Ho:YAG laser-induced liquid jet", The Journal of Japan Society For Laser Surgery and Medicine, No. 3, vol. 22, 2001, pp. 217-218, and English translation.

(Continued)

*Primary Examiner*—Henry M Johnson, III
*Assistant Examiner*—Aisha Hunte
(74) *Attorney, Agent, or Firm*—Buchanan Ingersoll & Rooney PC

(57) ABSTRACT

A laser induced liquid jet generating device comprising: a main body 6 adapted to be filled with a specified laser beam absorbing liquid and configured such that it can contain a laser irradiating part 4 of an optical fiber from which laser beams are emitted to generate jet streams J of said liquid W by irradiating said liquid W with laser beams, with said jet streams J ejected from said main body 6 to the outside; said main body 6 comprising: a catheter mounting unit mounted integrally or in a removable manner on a catheter member 13 into which said jet stream J is introduced; a jet generating tube unit 10 in which said laser irradiation part 4 is adapted to be positioned; and a heat transfer inhibition means 11 for inhibiting thermal effect due to laser beams irradiated by said laser irradiating part 4 from being transferred outside through said jet generating tube unit 10. Thus, it provides a laser induced liquid jet generating device that is safe for both the operator and the patient as it can apply irradiation of powerful laser beams for a long period of time without the catheter being thermally affected by the laser beams.

15 Claims, 19 Drawing Sheets

U.S. PATENT DOCUMENTS

| | | | |
|---|---|---|---|
| 6,406,486 | B1 | 6/2002 | De La Torre et al. |
| 6,440,124 | B1 | 8/2002 | Esch et al. |
| 6,669,685 | B1 * | 12/2003 | Rizoiu et al. .................. 606/10 |
| 7,344,528 | B1 * | 3/2008 | Tu et al. ........................ 606/7 |
| 2001/0037106 | A1 | 11/2001 | Shadduck |
| 2003/0009157 | A1 | 1/2003 | Levine et al. |

FOREIGN PATENT DOCUMENTS

| | | |
|---|---|---|
| EP | 1 532 936 A1 | 5/2005 |
| JP | 2003-111766 | 4/2003 |
| WO | 00/04838 | 2/2000 |
| WO | WO 02/26150 A1 | 4/2002 |

OTHER PUBLICATIONS

Nakagawa, Atsuhiro, et al., "Holmium: YAG Laser-Induced Liquid Jet Knife: Possible Novel Method for Dissection," Lasers in Surgery and Medicine, 2002, pp. 129-135, vol. 31, No. 2, Wiley-Liss, Inc., USA.

Extended European Search Report (EPO Form 1507N, EPO Form 1503 03.82(PO4C01), EPO Form PO 459) and accompanying European Search Opinion (EPO Form 1703 07.05CSX), issued in corresponding European Patent Application No. 06 006 392.2, Jul. 9, 2007; EPO, Munich, DE.

\* cited by examiner

LASER INDUCED LIQUID JET GENERATING DEVICE

This application is based on Patent Application No. 2005-95138 filed on Mar. 29, 2005 in Japan and Patent Application No. 2006-031214 filed on Feb. 8, 2006 in Japan, the content of which is hereby incorporated by reference.

BACKGROUND DISCUSSION

1. Field of the Invention

The present invention relates to a laser induced liquid jet generating device that generates a jet stream by irradiating liquid with a laser beam.

2. Description of the Related Art

As a way of treating thrombosis, i.e., a condition in which human blood vessels are obstructed, a treatment method of physically pulverizing matter causing thrombosis with a liquid jet stream has been discovered in recent years. This treatment method is highly appreciated as a very promising treatment method for thrombosis as it is not necessary to administer thrombolytic agents in large quantities which can cause serious adverse effects such as bleeding. Also an earlier resumption of blood flow is possible compared to a case of using thrombolytic agents only. In particular, while it is believed that the accompanying nerve symptom becomes difficult to be improved if an ischemic condition lasts for more than six hours, an extremely high recovery effect can be expected if the resumption of blood flow occurs within a few hours of the crisis.

Unexamined Publication No. JP-A-2003-111766 (refer to sections 0014, 0015, and FIG. 1), Unexamined Publication No. JP-2002-521084 corresponding WO00/04838 (refer to sections 0004, 0010, 0096, and FIG. 27), and JJSLM (THE JOURNAL OF JAPAN SOCIETY FOR LASER SURGERY AND MEDICINE) No. 3, Vo. 22 (2001) (refer to p. 217) disclose a method of introducing a pulsing laser beam from a laser oscillator into an optical fiber inserted into a catheter in order to rapidly heat physiological saline solution that fills said catheter, induce a liquid jet stream, thus to crush and remove thrombi and the like with the force of the liquid jet stream.

In this method, a catheter in which an optical fiber is inserted, is brought to the vicinity of a thrombus before a liquid jet stream is generated in order to intensify the treatment effect by minimizing the depreciation of the force of the liquid jet stream.

A traditional catheter is a long, small diameter tube made of such materials as polypropylene and polyimide, generally flexible in order to be able to deform easily in accordance with winding blood vessels and tends to absorb the laser beam easily as described in Unexamined Publication No. JP-A-2002-521084 (WO00/04838), so that it tends to be affected thermally when it is subjected to intense laser beams.

When an optical fiber with an outside diameter (core diameter) of approximately 0.4 mm is inserted into a flexible catheter made of such a material with a small diameter (normally 0.9 mm), it is common that only an extremely small clearance exists between the inner surface of the catheter and the outer surface of the optical fiber. If a strong laser beam irradiation is applied under this condition, the heat of the laser beam is transmitted to the catheter, and the laser beam's energy is absorbed by the catheter's material to cause melting or deformation of the catheter. This may hinder the liquid jet stream from being ejected smoothly and shorten the life of the catheter itself. There is also a concern that the heat that melts or deforms resins or metals may affect blood vessels as well.

For these reasons, it has also been considered that the area for generating a strong liquid jet stream by an irradiating laser beam should not be located inside of the catheter which is inserted into a blood vessel, but rather should be located on the outside of the proximal part of the catheter, i.e., outside of the catheter. However, it is necessary in that case to use a laser irradiation of a higher power to generate a liquid jet stream of the same strength as the aforementioned method because the distance from the laser irradiation part to the catheter tip becomes longer than the aforementioned method. As a consequence, the vicinity of the laser irradiation part becomes substantially hot. Patients and operators who accidentally touch the laser irradiation part that has turned very hot can get burned. A high power laser beam and the high temperature caused by it can expedite the deterioration of the material in the neighborhood of the laser irradiation part, eventually damaging the device. Moreover, if a drug solution containing a drug such as thrombi solvent is used as the liquid to be irradiated with a laser beam to generate a jet stream, the high heat generated as a result of the laser irradiation may reduce or eliminate the efficacy of the drug in the drug solution.

Consequently, problems have arisen in minimizing how to minimize the effect of the heat generated by the laser irradiation on the outside of the catheter.

SUMMARY

A laser induced liquid jet stream generating device is relatively safe for patients and operators because the catheter is protected from the laser beam's thermal effect, thus allowing long time of irradiation with a high power laser beam.

The laser induced liquid jet stream generating device has a main body that is to be filled with a specified liquid to absorb the laser beam and the main body is equipped with a laser irradiation part of an optical fiber through which the laser beam from a laser generator is guided. The laser induced liquid jet stream device irradiates said liquid with the laser beam emitted from the laser irradiating part to cause said liquid to generate a jet stream, which is ejected outside from the main body. The main body of the laser induced liquid jet stream device comprises a catheter mounting unit, a jet generating tube unit, and heat transfer inhibition means. The catheter mounting unit is mounted integrally or in a removable manner on a catheter member to which said jet stream is introduced. The jet generating tube unit encases said laser irradiating part internally and generates said jet stream. The heat transfer inhibition means makes sure that the thermal effect from the laser beam irradiated from said laser irradiating part does not extend externally via said jet generating tube unit.

The device does not irradiate the laser beam in a narrow catheter but irradiate the laser beam in the jet generating tube unit provided at the proximal part of the catheter and introduce the generated liquid jet stream from the tip of the jet generating tube unit into the catheter, so that it is possible to use a thinner catheter as it no longer needs to have a space inside the catheter for inserting the optical fiber, thus allowing higher powered laser beam irradiation.

Moreover, since a heat transfer inhibition means is provided outside of the jet generating tube unit for preventing the thermal effect that is caused by the laser irradiating part, the heat is not transmitted to the outside even if a high power laser irradiation is applied, so that it is safe for patients and operators. Further, it provides an improved operating maneuverability, and enables to perform extremely powerful thrombi destruction operation more securely and for long hours. Furthermore, even if a drug solution is used, cooling the vicinity of the laser irradiation part of the jet generating tube unit effectively prevents the temperature of the drug solution in the vicinity to rise excessively and maintains the activity of the drug solution without being affected.

DETAILED DESCRIPTION

Various embodiments of the device at issue here will be described in detail in the following with reference to the accompanying drawings:

First Embodiment

Figure 1:
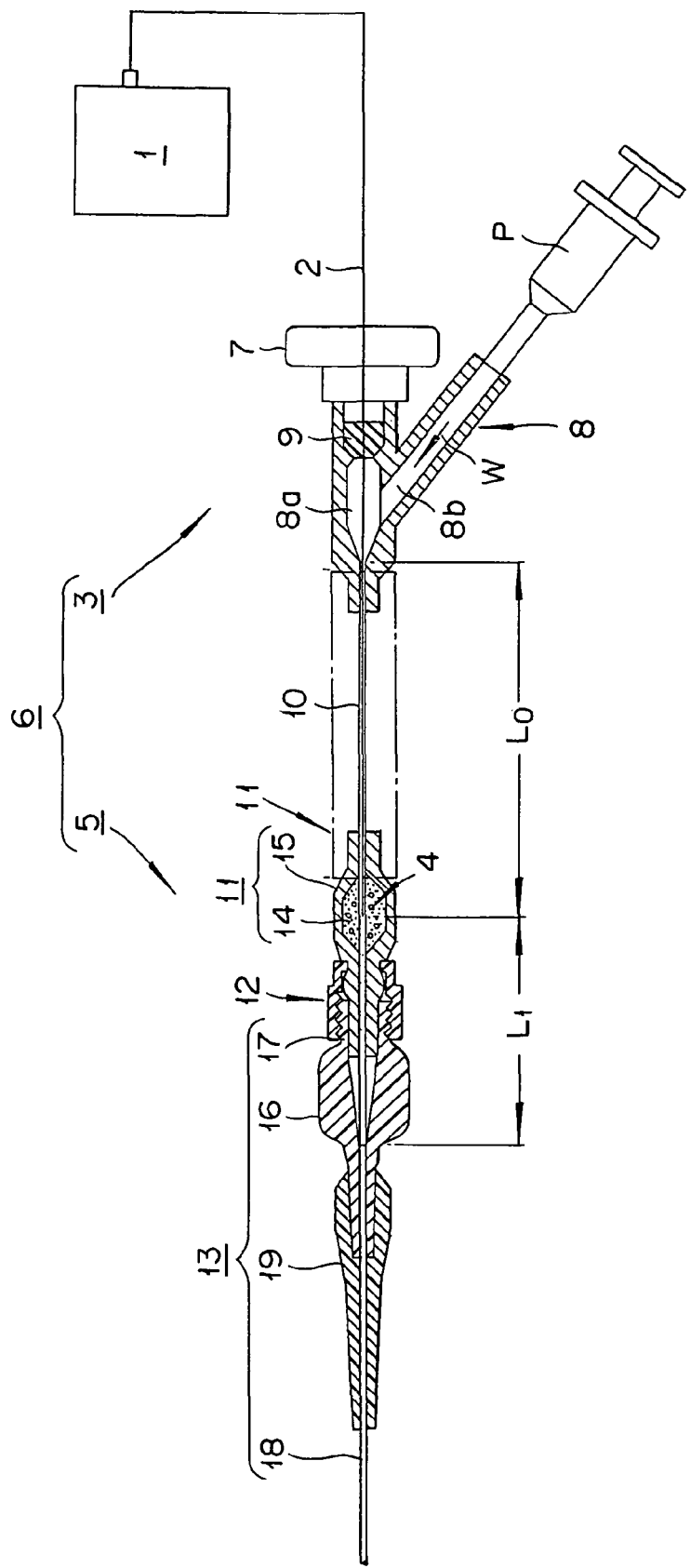
FIG. 1 is an outline cross-sectional drawing of a first embodiment.

In FIG. 1, the laser induced liquid jet stream device of this embodiment generally includes a laser oscillator 1, an optical fiber 2 connected to the laser oscillator 1, and a main body 6. The main body 6 includes a base unit 3 for allowing the optical fiber 2 to penetrate through to hold it, and an operating unit 5 in which a laser irradiating part 4, namely a tip part of the optical fiber 2 extended from the base unit 3, is contained inside of a jet generating tube unit 10.

Since it is preferable to use a long jet generating tube unit 10 to make it possible to materialize a high power laser irradiation, the base unit 3 and the operating unit 5 are made separate from one another. Since the laser generator 1 and the optical fiber 2 are publicly known, a detail description of such features is not provided.

A detailed description of the other aspects of the device follows. First, in the base unit 3 of the main body 6, a so-called "Y-connector" 8 is screwed on to the distal end of a connecting member 7 that is connected to the laser oscillator 1, and an elastically deformable valve body 9 is provided at a first port 8a of the Y-connector 8, so that the optical fiber 2 internally inserted into the valve body 9 can be maintained in a fixed condition by elastically pressuring the volve body 9 from the outside or in a relaxed condition depending on the threading condition between the connecting member 7 and the Y-connector 8. A second port 8b is adapted to be fluidly connected to a liquid injection member P such as a syringe pump for injecting a specified liquid W (shown by a solid line arrow), such as physiological saline solution and a drug solution of a drug such as thrombolytic agent.

The operating unit 5 of the main body 6 includes the jet generating tube unit 10, a heat transfer inhibition unit 11, a catheter mounting unit 12, and a catheter member 13 arranged generally in a linear manner starting from the proximal end (the side closer to the laser oscillator is called the proximal end and the side ejecting the jet stream J is called the distal side). The heat transfer prevention unit 11 constitute heat transfer means for inhibiting thermal effect due to laser beams irradiated by said laser irradiating part 4 from being transferred outside through jet generating tube unit 10.

The jet generating tube unit 10 is a thin straight tube, whose proximal end is connected to the Y-connector 8 of the base unit 3 and whose distal end extends towards pointing the inside of the catheter member 13. The optical fiber 2 is inserted in the jet generating tube unit 10, and the jet stream J is generated inside of said jet generating tube 10. Therefore, the jet generating tube unit 10 is preferably made of a metal tube (such as stainless steel) that has a relatively high heat resistance as it is subjected to high temperatures.

There is a possibility however that the inside of the jet generating tube unit 10 may discolor or deteriorate as it is difficult to completely suppress the alteration or deterioration of the tube made of stainless steel, etc. This is a phenomenon caused by absorption of a portion of the laser beam in the jet generating tube unit 10. In order to suppress this phenomenon, it is effective to provide a material with an excellent laser beam reflection rate substance at the inside of the jet generating tube unit 10, particularly in the vicinity of the optical fiber 2.

It is also effective to construct the jet generating tube unit 10 from a combination of stainless steel and a material with excellent laser beam reflection capability. The material having excellent laser beam reflection capability can be provided in the portion of the jet generating tube unit 10 in the vicinity of the laser irradiating part 4. Such material can then be connected at both ends to the other material (e.g., stainless steel). It is expected that the laser beam absorption and the accompanying alteration or deterioration of the jet generating tube unit 10 can be suppressed thus making it possible to increase the liquid jet power further. Although gold, platinum, silver, copper or aluminum can be considered as materials suitable for the light reflection layer, it is preferable to use gold or platinum as the main ingredient considering the safety of the organism. The thickness of the reflection layer is preferably as large as ten times of the specified laser wavelength, as the laser beam may pass through the layer if it is only several microns thick and cause deterioration of the base material and peeling off the reflection layer. It is also effective to provide mirror finish to the inside of the jet generating tube unit 10 including the reflection layer in improving the laser reflection rate.

The preferable material for the jet generating tube unit 10 can be, in addition to a metal tube (stainless steel, etc.) as mentioned before, anything as long as it possesses adequate mechanical strength, pressure resistance (non-compressive) and heat resistance to withstand the high pressure and high temperature that occur during the jet generation.

Moreover, in some cases, it is possible to construct the jet generating tube unit 10 to allow the laser beam to pass through and provide a mechanism to shut off the laser beam separately as described in the third through fifth embodiments.

The gap G (see FIG. 2) between the inner surface of the jet generating tube unit 10 and outer surface of the optical fiber 2, and the length $L_0$ (see FIG. 1) where the optical fiber 2 axially overlaps with the jet generating tube unit 10 (hereinafter called "overlapping portion" for simplicity sake) are determined in such a manner that the internal liquid W itself helps the jet stream J to move forward by inhibiting the jet stream J from being directed rearwardly. Making the gap G narrower and the length $L_0$ of the overlapping portion longer in such an arrangement, the resistance against the reverse flow of the jet stream J increases, so that it is possible to introduce a more powerful jet stream J into the catheter member 13. Moreover, the operator can control the strength of the jet stream J by adjusting the length $L_0$ of a portion where the optical fiber 2 overlaps with the jet generating tube unit 10.

Although the jet generating tube unit 10 is illustrated as being separate from other members in the example shown, the structure is not limited to this condition and a portion of the inside of the main body 6 can be formed as a tubular configuration forming the jet generating tube unit 10 so long as it has the capability to withstand the high temperature and the high pressure caused by the laser irradiation.

The laser irradiating part 4 is preferably located at a predetermined distance of L1 from the distal end of the jet generating tube unit 10. Such an arrangement causes the jet stream J generated inside the jet generating tube unit 10 to be powerfully ejected toward the ejection port of the main body 6 without being unnecessarily weakened.

The optical fiber 2 should be located in such a manner that the distal end of the optical fiber 2 is located as close as possible to the center of the lumen of the jet generating tube unit 10 so that a stable liquid jet output is obtained while suppressing the deterioration of the jet generating tube unit 10. More specifically, it is preferable to have a radial protrusion (not shown) at a height that corresponds to one half or less of the difference between the outer diameter of the optical fiber 2 and the inner diameter of the jet generating tube unit 10 at a part of the lumen of the aforementioned overlapping portion of the jet generating tube unit 10. This makes it possible to maintain the specified transport of the liquid W and to locate the laser irradiating part 4 generally at the center of the lumen of the jet generating tube unit 10 so that the laser irradiation can be suppressed at the eccentric position. It is preferable to provide the radial protrusion at two or more locations so that they can support the optical fiber 2 generally evenly inside the jet generating tube unit 10. However, the optimum number of radial protrusions should be 2-4 considering the transportation resistance of the liquid W.

Although the outer diameter of the optical fiber 2 and the inner diameter of the jet generating tube unit 10 are not limited specifically, it is preferable to choose the inner diameter of the jet generating tube unit 10 to be 1.05-1.50 times the outer diameter of the optical fiber 2, the length $L_0$ of the overlapping portion to be 30-150 mm, the outer diameter of the optical fiber 2 to be 600-800 µm, and the inner diameter of the jet generating tube part 10 to be 700-1000 µm in order to generate liquid jet stream J in a lower viscosity liquid such as water or physiological saline solution. However, it is preferable to increase the gap between the inside surface of jet generating tube unit 10 and the outside surface of the optical fiber 2 from the standpoint of liquid transport resistance if the jet stream J is to be generated in a high viscosity liquid such as contrast media. It is preferable to choose the distance L1 between the distal end of the jet generating tube unit 10 and the distal end of the optical fiber 2 (laser irradiating part 4) to be 25-120 mm.

The heat transfer inhibition unit 11 of this embodiment is constructed by covering the outer periphery of the vicinity of the laser irradiating part 4 provided in the jet generating tube unit 10 with a heat insulating member 14, and is connected to jet generating tube unit 10. However, the heat transfer inhibition unit 11 can be constructed to cover the entire exposed portion of the jet generating tube unit 10 as shown in FIG. 1 with a single-dot chain line so that the thermal effect of the jet generating tube unit 10 can be prevented from being transmitted outside.

The heat transfer inhibition unit 11 can also include a capsule-like outer cover member 15 covering the heat insulting member 14. Alternatively, the heat transfer inhibition unit 11 can be a capsule-like outer cover member whose inside is under vacuum, or can be a heat insulating material attached to the outer periphery of the jet generating tube unit 10. In other words, the heat transfer inhibition unit 11 of this specification should be construed to mean not only a material that simply inhibits heat transfer, but also more widely thermal conductivity inhibition structures such as those described above.

It is preferable to have the capsule type outer cover member 15 constructed of a material with heat resistance to a degree, such as stainless steel. If a material with heat resistance is used as the outer cover member 15, it is not necessary to form the jet generating tube unit 10 separate from the heat transfer inhibition unit 11, but rather it can be formed as a part of the heat transfer inhibition unit 11.

The catheter member 13 comprises a catheter hub 16, a connecting tube unit 17 provided on the proximal side of the catheter hub 16, a generally thin and long tube 18 provided on the distal side of the catheter hub 16, and a kink-resistant protector 19 provided on a portion of the external periphery of the catheter hub 16 and the tube 18.

The catheter member 13 and the outer cover member 15 are connected by a removable catheter mounting unit 12. The inner surface of the connecting pipe unit 17 of the catheter member 13 is generally formed in a tapered shape so that press-fitting an end section 15a of the outer cover member 15 into the catheter member 13 causes the catheter member 13 tube fit with the outer cover member 15 in a liquid-tight manner.

Figure 2:
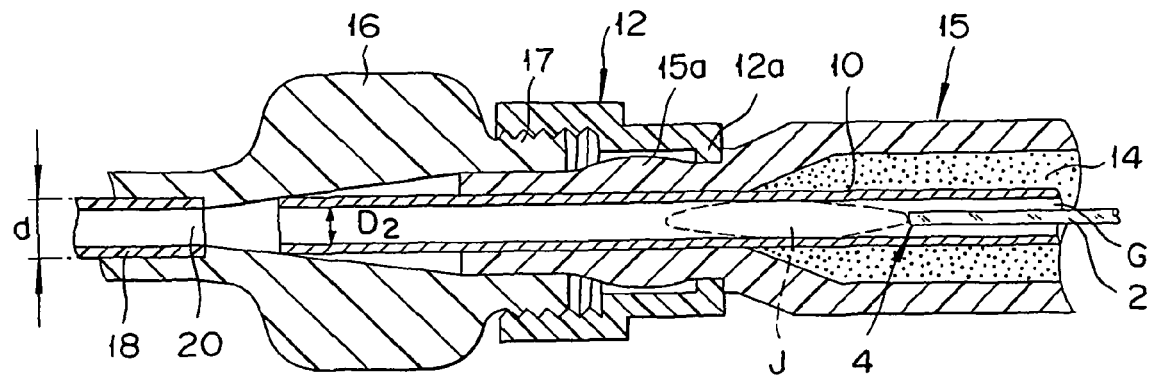
FIG. 2 is a cross section of a variation of the jet generating tube unit with an enlarged view of the key area of FIG. 1.

Also, the catheter mounting unit 12 is made of a substantially cylindrical member as shown in FIG. 2, wherein its distal end side is connected with connecting tube unit 17 (e.g., in a screw-threaded engagement). An inner protrusion 12a formed on the proximal side of the catheter mounting unit 12 fits with a part of the outer cover member 15, adjacent a portion where the outer cover member 15 is bulging outward. Therefore, the catheter mounting unit 12 is temporarily held by the bulging area as the outer cover member 15 is inserted and then firmly connected by the screw connection at a fixed position. However, the catheter mounting unit 12 can also be constructed as an integral part of the outer cover member 15 or the catheter member 13.

It is preferable in the catheter member 13, in particular, that the jet stream J ejected from the distal end of the jet generating tube unit 10 flows in without power loss. Therefore, a jet stream induction port 20 of the catheter member 13 and the distal end of the jet generating tube unit 10 are arranged to face each other concentrically. This makes it possible to connect the jet stream induction port 20 of the catheter member 13 with the distal end of the jet generating tube unit 10 in an essentially liquid-tight manner so as to minimize the power loss of the jet stream J sent from the jet generating tube unit 10, making it easier to introduce the power of the liquid jet stream caused by the irradiation of laser beams into the catheter.

Although it is preferable that the jet generating tube unit 10 and the catheter member 13 abut each other, they can be slightly spaced apart so that the jet stream J does not lose output essentially.

It is preferable that the inner diameter "d" of the jet stream induction port 20 of the catheter member 13 and the inner diameter D2 of the jet generating tube unit 10 can be made equal so as to minimize the power loss of the jet stream J.

Figure 3:
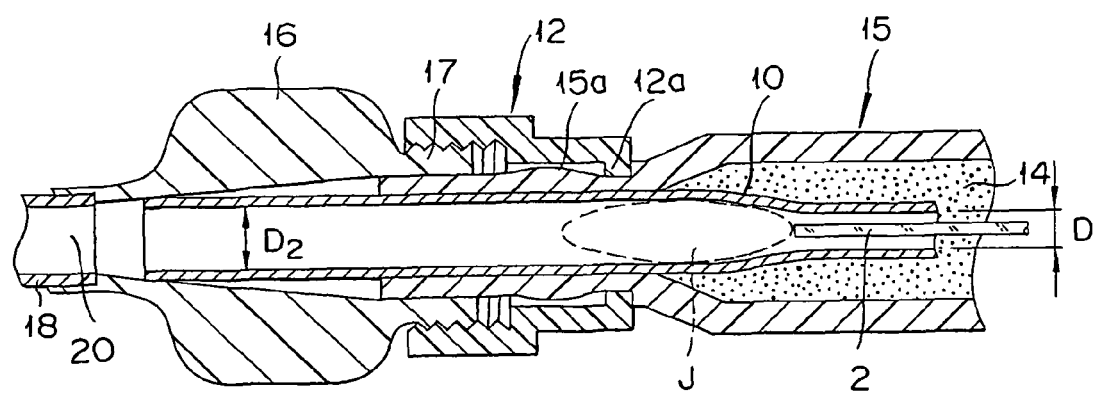
FIG. 3 is an enlarged cross section of the key area showing another variation of the jet generating tube unit.

Furthermore, if the jet generating tube unit 10 is designed in a trumpet-shape as shown in FIG. 3, the diameter of the distal end of the jet generating tube unit 10 expands, so that it makes a tight contact with the inner surface of the connecting tube unit 17 through the outer cover member 15, the jet generating tube unit 10 makes a more secure contact with the catheter member 13, making a more preferable condition.

FIGS. 4 through 9 show various structural examples of the distal end of the jet generating tube unit 10. In order to suppress the output loss of the liquid jet J as much as possible, it is important to minimize the gap that might cause the loss of the liquid jet stream J when the catheter member 13 and the heat insulating member 14 are connected using the catheter mounting unit 12.

Figure 4:
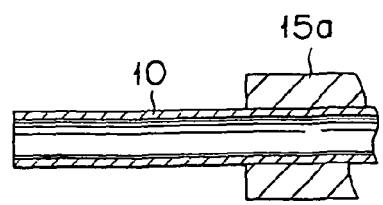
FIG. 4 is an outline cross section showing a structural example of the distal end of the jet generating tube unit.
Figure 5:
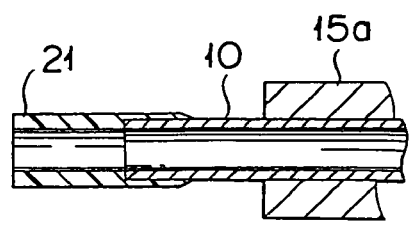
FIG. 5 is an outline cross section showing a structural example of the distal end of the jet generating tube unit.

FIG. 4 is an example of a construction of the distal end of the jet generating tube unit when the jet generating tube unit 10 makes a direct contact with the catheter hub 16. This construction example is advantageous from the cost standpoint as it has a simpler structure. However, one concern with this construction is that the distal end of the jet generating tube unit 10 can damage the lumen of the catheter hub when the hub is connected with the jet generating tube unit 10. Therefore, a protection member 21 made of a soft material can be provided at the distal end of the jet generating tube unit 10 as shown in FIG. 5.

Figure 6:
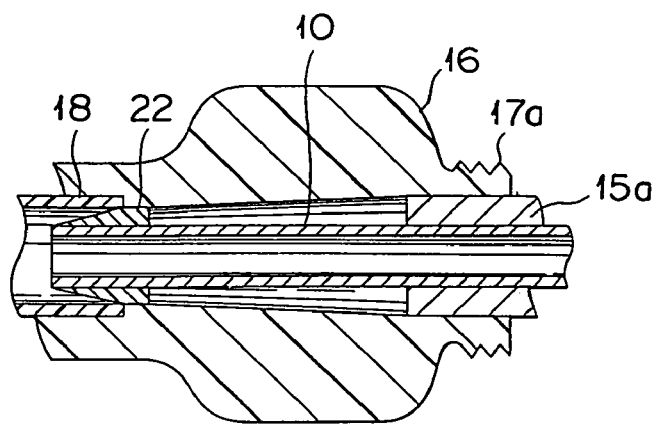
FIG. 6 is an outline cross section showing a structural example of the distal end of the jet generating tube unit.

FIG. 6 is a structural example where a gap inhibition member 22 made of a soft material is provided at the distal end of the jet generating tube unit 10 to plug the gap between it and the lumen of the catheter member 13. For example, if the lumen of the catheter member 13 is larger than the outer diameter of the jet generating tube unit 10, the gap inhibition member 22 provided at the distal end of the jet generating tube unit 10 improves the contact between it and the lumen of the catheter member 13 and prevents damage to the catheter hub 16 at the same time.

Figure 7:
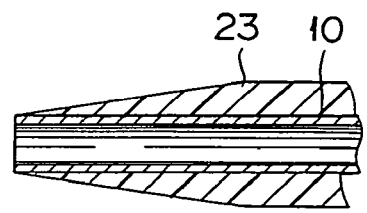
FIG. 7 is an outline cross section showing a structural example of the distal end of the jet generating tube unit.

FIG. 7 is a structural example where a cover member 23, which is made of a material (synthetic resin, etc.) similar to the material used for outer cover member 15, covers the jet generating tube unit 10 in order to reinforce the jet generating tube unit 10. If the outer surface of the cover member 23 is made into a tapered shape, the contact between it and the lumen of the catheter member 13 can also be improved.

Figure 8:
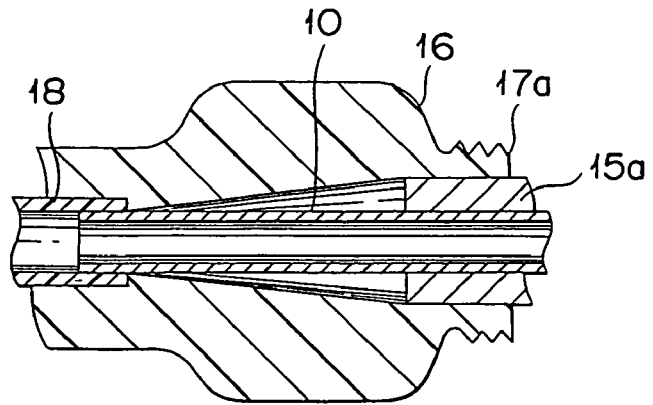
FIG. 8 is an outline cross section showing a structural example of the distal end of the jet generating tube unit.
Figure 9:
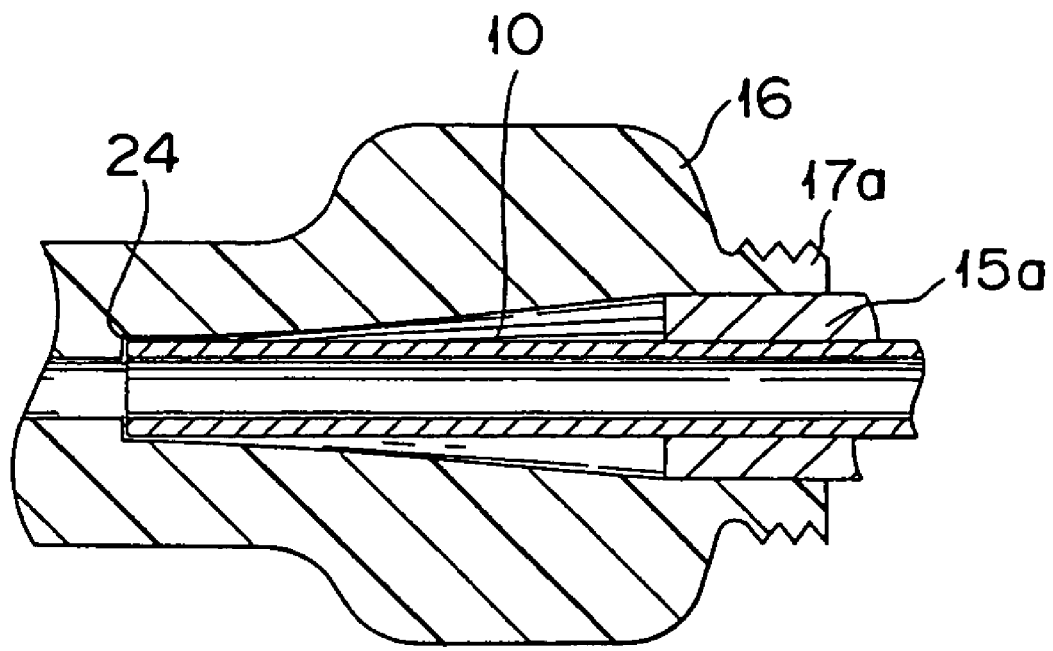
FIG. 9 is an outline cross section showing a structural example of the distal end of the jet generating tube unit.

FIG. 8 is a structural example wherein the distal end of the jet generating tube unit 10 is either placed closer to or simply inserted into the lumen of the tube 18 without making it a force-fitting concern with the catheter member 13. FIG. 9 is a structural example wherein a step 24 is formed in the lumen of the catheter hub 16 so as to fit the distal end of the jet generating tube unit 10. This also makes it possible to cause the jet flow J into the tube 18.

However, if there is a large diameter difference between the distal end of the jet generating tube unit 10 and the lumen of the tube 18 or the catheter hub 16 in the cases shown in FIGS. 8 and 9, it may cause an output loss. Thus, it is preferable that the diameter difference between the outer diameter of the distal end of the jet generating tube unit 10 and the inner diameter of distal end of the catheter hub 16 is less than 100 μm. Moreover it is preferable that the diameter difference between the inner diameter of the distal end of the jet generating tube unit 10 and the inner diameter of the tube 18 is less than 100 μm.

Figure 10:
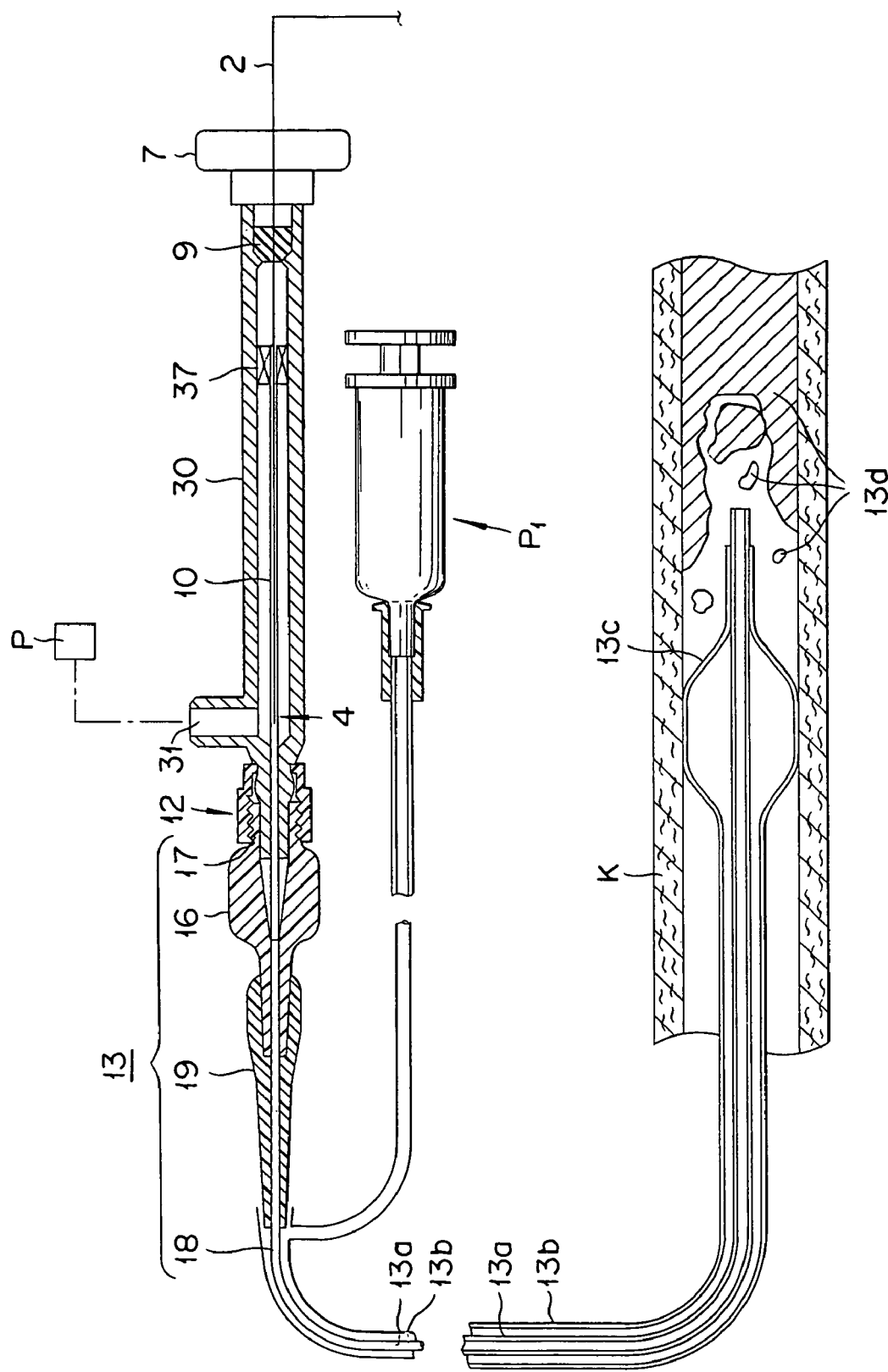
FIG. 10 is an outline cross-sectional drawing of another example of the catheter member.

FIG. 10 is another example of the catheter member. The distal end area of the catheter member is shown enlarged in FIG. 10, and the members common to those in FIGS. 1 and 2 are labeled in the similar manner to omit the description.

The catheter member 13 has an inner tube 13a and an outer tuber 13b as shown in FIG. 10, and the distal end of the outer tube 13b is jointed to the inner tube 13a to seal between them, so that when the liquid W is supplied by a syringe P1 between the inner tube 13a and the outer tube 13b, the distal end of the outer tube 13b expands to form a balloon unit 13c. If such a balloon part 13c can be inflated in a blood vessel, the jet stream ejection part which is the distal part of the catheter member 13 can be held immobile, incapable of moving backward, so that the operation of setting up the jet stream ejecting part in the center of a blood vessel K, i.e., the positioning operation, is made easier thus improving the operator's operation. It is also possible to stop the blood flow so that a crushed thrombus 13d does not move arbitrarily.

The following is a description of the operation of the device described above.

First, the inside of the catheter member 13 is primed. When the liquid W (a laser beam absorbing liquid) is injected into the Y-connecter 8 via a second port 8b of the Y-connecter 8, the liquid W flows through the route of the second port 8b of the Y-connecter 8→a first port 8a→the jet generating tube unit 10 and flows out from the distal end of the jet generating tube unit 10. This signals that the main body 6 is filled with the liquid W, thus completing its priming operation.

After the priming operation is complete, a guide wire (not shown) is inserted into the catheter member 13, and the catheter member 13 is transported to the target position of the vessel by guiding it with the guide wire. When the catheter member 13 has arrived at the target position, the guide wire is removed from the catheter member 13.

Next, the end section 15a of the outer cover member 15 is inserted into the catheter hub 16 of the catheter member 13, and the catheter member 13 and the outer cover member 15 are jointed together in a liquid-tight manner by the catheter mounting unit 12. The liquid W is then transported by the liquid injection member P, the optical fiber 2 is inserted through the valve body 9 passing through the first port 8a, and is stopped when its distal end, i.e., the laser irradiating part 4, reaches the desired position inside of the jet generating tube unit 10. At this time, the laser irradiating part 4 is located at a specified distance L1 from the distal end of the jet generating tube unit 10. As a result, the heat transfer inhibition unit 11 at the outer surface of the jet generating tube unit 10 is located at a position corresponding to the axial position of the laser irradiating part 4. When the Y-connector 8 is twisted into the connecting member 7 at this stage, the valve body 9 is deformed by compression, and the position of the optical fiber 2 in the jet generating tube unit 10 is fixed.

In this embodiment, the position of the optical fiber 2 in the jet generating tube unit 10 is determined by taking into account that the output of the jet stream J from the distal end of the device can be adjusted through adjustment of the reverse flow of the jet stream J by means of adjusting the length $L_0$ of the portion where the optical fiber 2 overlaps with the jet generating tube unit 10. In other words, by adjusting the position of the optical fiber 2 that is sliding it longitudinally slid within the jet generating tube unit 10 by tightening or loosening the valve body 9 with the Y-connector 8.

The optical fiber 2 is connected with the laser oscillator 1, and the laser oscillator 1 is operated, so that the liquid W supplied towards the tube 18 is irradiated with the pulsing laser beam from the laser irradiation part 4. Since this irradiation occurs not in the tube 18 of the catheter member 13, but in the jet generating tube unit 10, it causes violent evaporation of the liquid W in the jet generating tube unit 10 generating bubbles. The bubbles generated intermittently due to the irradiation of the pulsing laser beam rapidly and drastically increase pressures and purge the liquid W in the jet generating tube unit 10, causing the liquid jet stream J.

Since the distal end of the jet generating tube unit 10 and the jet stream induction port 20 of the catheter member 13 are facing each other in this embodiment, the generated liquid jet stream J is quickly propagated through the liquid W in the tube 18, causing the liquid W in the tube 18 to be ejected toward the thrombus ahead. This causes the thrombus in the blood vessel to be crushed due to a powerful liquid jet stream J. Blood flow circulation restriction associated with the thrombus is thus removed. As the crushing of the thrombus is confirmed, the optical fiber 2 is retracted from the jet generating tube unit 10, a suction device such as a syringe is attached to the second port 8b of the Y-connector 8, and the crushed thrombus is taken out together with the liquid W. The crushed thrombus can be sucked out via the lumen of a guide catheter (not shown) which is provided to guide the catheter member 13 together with the guide wire to the destination area of the blood vessel.

<First Variation>

Figure 11:
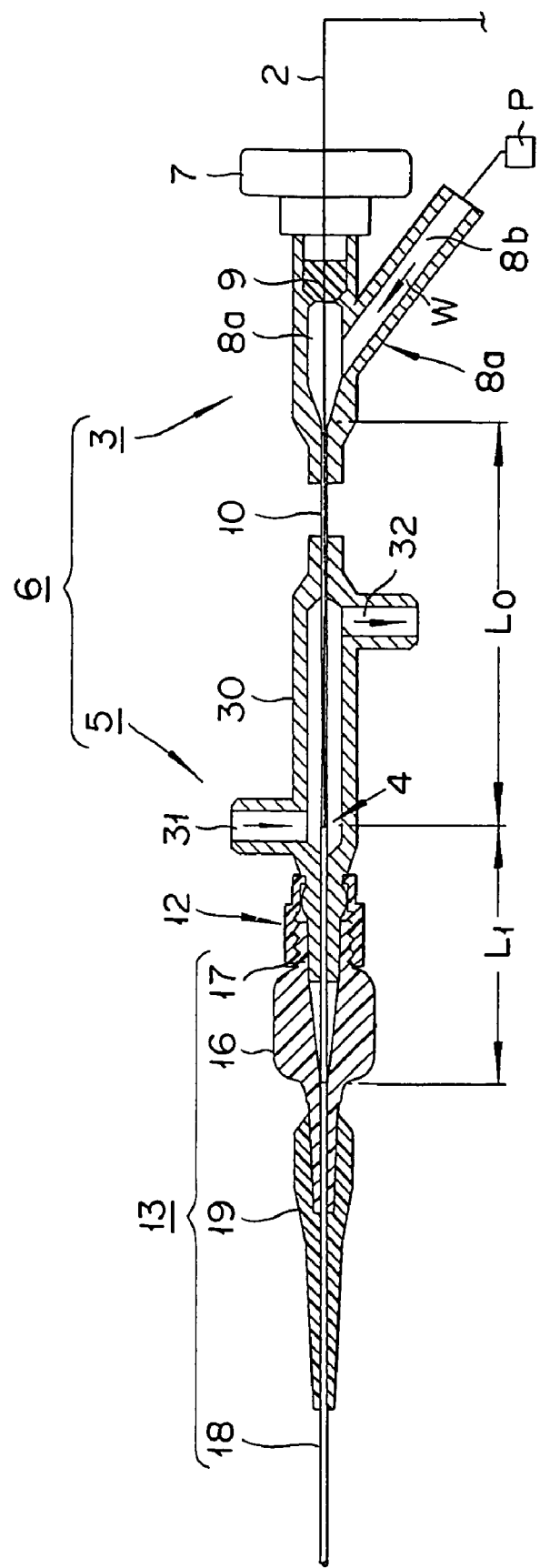
FIG. 11 is an outline cross-sectional drawing of a first variation of the first embodiment of the invention.

FIG. 11 is the first variation of this embodiment. Those members common to those in FIGS. 1 and 2 are labeled in the similar manner to omit the description.

As mentioned above, the heat transfer inhibition unit 11 can be capsule-shape including the heat insulating member 14 covered with the outer cover member 15. However, the heat transfer inhibition unit 11 can alternatively be a device that is cooled by running a cooling liquid. Although such a cooling liquid can be tap water, it is preferable to use the specified liquid W used for generating the liquid jet. The temperature of the cooling liquid is sufficient so long as it can cool the jet generating tube unit 10. Although not limited in this regard, it is preferable that the temperature of the cooling liquid be equal or lower than the normal room temperature (25° C.).

The heat transfer inhibition unit of this variation is provided to cover the jet generating tube unit 10 over a wide area and includes a duct 30 through with the cooling liquid runs. The duct 30 has a inlet 31 at the distal end through which the cooling liquid enters, and an outlet 32 at the proximal end through which the cooling liquid exits, wherein the inlet 31 is provided at a location that corresponds with the laser irradiation part 4 or ahead of it. Therefore, the cooling liquid can be tap water since it does not flow into the jet generating tube unit 10 and used only for the purpose of cooling the jet generating tube unit 10.

With such an arrangement, the cooling liquid that enters through the inlet 31 cools first of all the laser irradiation part 4 and its vicinity where the temperature gets highest inside the jet generating tube unit 10 and then flows along the periphery of the jet generating tube unit 10 to exit through the outlet 32, so that cooling can be done efficiently for a wide range. Moreover, the jet generating tube unit 10 can be continuously cooled by running the cooling liquid continuously so that the system can be used for a long time and the operator can concentrate on the operation of crushing thrombi without worrying about the safety of the system.

Second Embodiment

Figure 12:
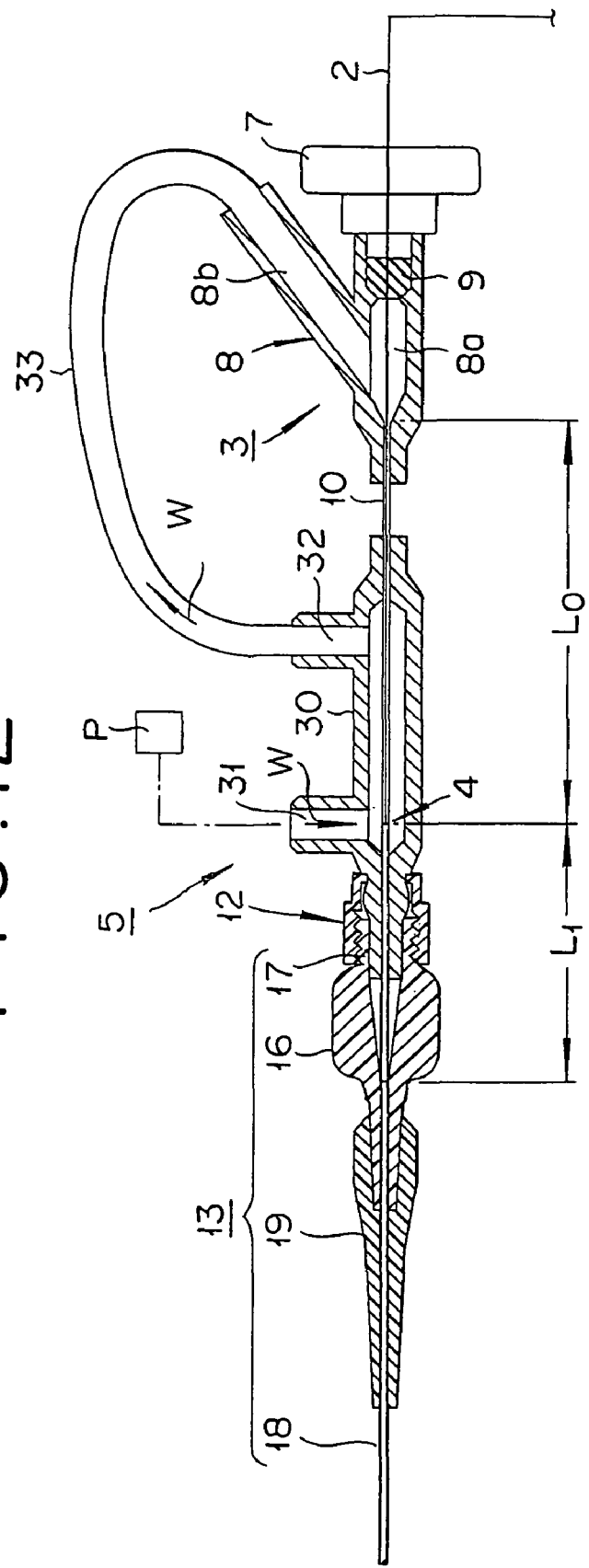
FIG. 12 is an outline cross-sectional drawing of a second embodiment.

FIG. 12 shows the second embodiment of the invention. Those members common to those in FIG. 1 are labeled in the similar manner to omit the description.

Although different flow passages are used for the cooling liquid intended for cooling the jet generating tube unit 10 and the liquid to be introduced into the inside of the jet generating tube unit 10 in the first variation of the previous embodiment, the cooling liquid is introduced into the jet generating tube unit 10 in this embodiment.

As can be seen in FIG. 12, the duct 30 is constructed in such a way that the inlet 31 is located at a position corresponding with the laser irradiation part 4, the outlet 32 is located to open upward on the proximal side of the duct 30, and a guide tube 33 provided at the outlet 32 guides the liquid W that flows out to the inside of the jet generating tube unit 10.

With such an arrangement, since the cooling liquid is guided directly to the jet generating tube unit 10, the operator's benefits further increase as the system can be used continuously for a long time.

In this embodiment as well, the tightening of the Y-connector 8 allows the position of the optical fiber 2 to be adjusted and fastened inside the jet generating tube unit 10 by the valve body 9, which in turn allows the adjustment of the length $L_0$ of a portion where the optical fiber 2 overlaps with the jet generating tube unit 10, the adjustment of the reverse flow of the jet stream J, and consequently the adjustment of the output of the jet stream J from the distal end of the device.

<First Variation>

Figure 13:
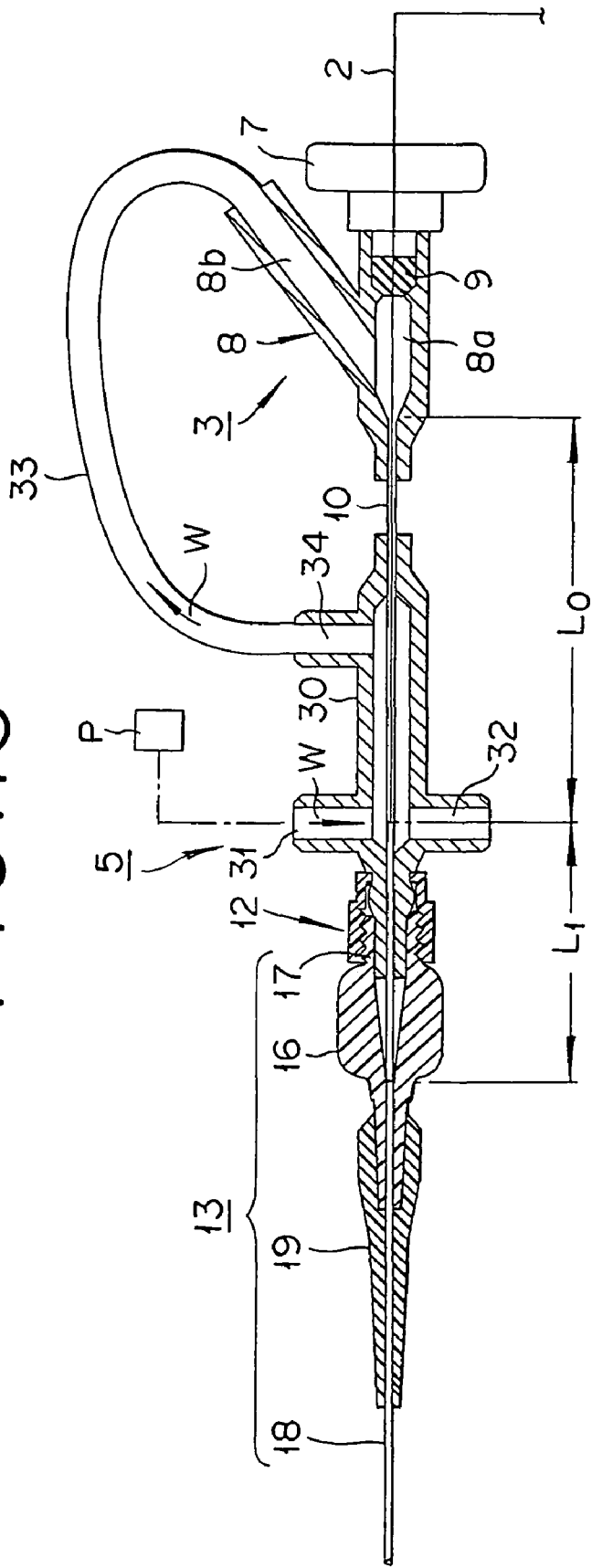
FIG. 13 is an outline cross-sectional drawing of a first variation of the second embodiment.

FIG. 13 shows a first variation of the second embodiment of the invention. Those members common to those in FIGS. 1 and 11 are labeled in the similar manner to omit the description.

The cooling liquid is also guided into the jet generating tube unit 10 in this first variation, the duct 30 here is so constructed that both the inlet 31 and the outlet 32 are provided in the area that corresponds with the laser irradiation part 4, so that the cooling liquid is guided into the jet generating tube unit 10 via the guide tube 33 through a second outlet 34 provided separately on the proximal side of the duct 30.

With such an arrangement, the laser irradiation occurring inside the jet generating tube unit 10 can be met with an improved cooling effect of the jet generating tube unit 10 as the cooling liquid that flows in through the inlet 31 flows out immediately through the outlet 32 thus increasing the volume of the cooling liquid flow inside the duct 30. Moreover, since the cooling liquid is used by introducing it into the jet generating tube unit 10, there is no need to inject the liquid W independently by means of a syringe pump and the like so that the operator's benefits are further improved allowing the use of the system for a long time. This variation provides the same features as said embodiment in that the destruction of thrombi can be done powerfully and securely.

<Second Variation>

Figure 14:
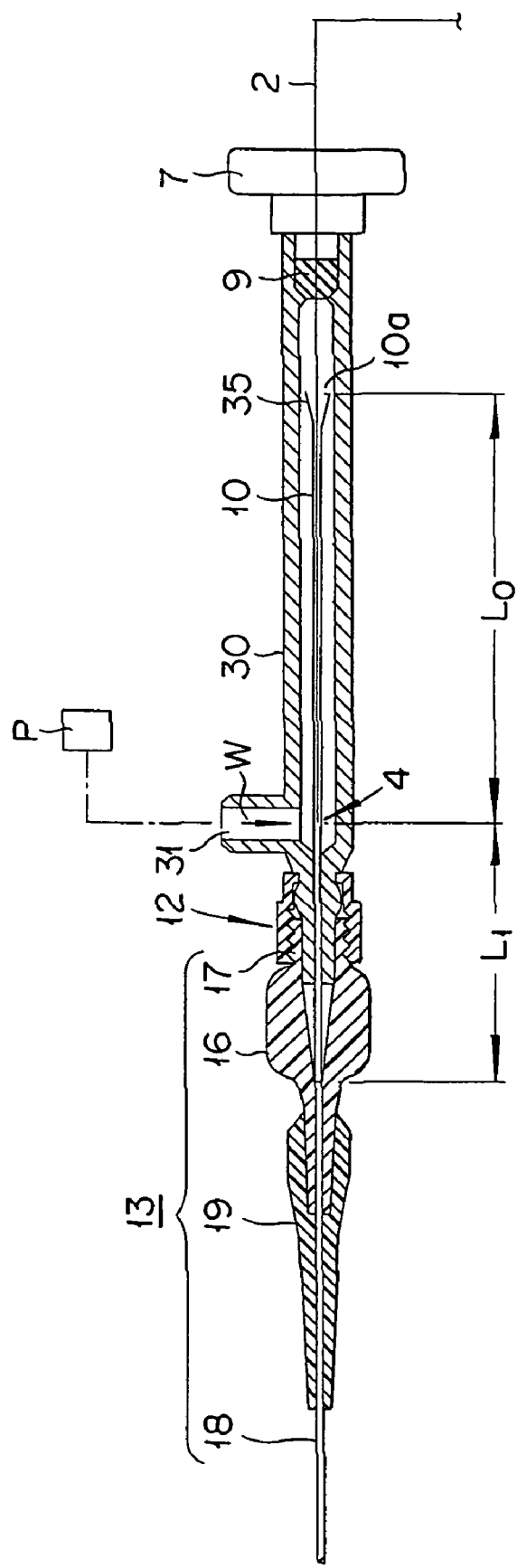
FIG. 14 is an outline cross-sectional drawing of a second variation of the second embodiment.

FIG. 14 is the second variation of this embodiment. Those members common to those in the previously mentioned drawings are labeled in the similar manner to omit the description.

While the base unit 3 of the main body 6 and the operating unit 5 are formed separately for introducing the cooling liquid into the jet generating tube unit 10 in said second embodiment, the duct 30 is connected to the connecting member 7 directly and the jet generating tube unit 10 is completely contained in the duct 30 in this variation.

The duct 30 of this variation is constructed in such a way that its one end is connected to the catheter member 13, while the other end is connected to the connecting member 7, thus containing the jet generating tube unit 10 in its inside completely, so that only the inlet 31 is provided at a location corresponding with the laser irradiation part 4 or a head (distal side) of the laser irradiation part 4, allowing the cooling liquid entering through the inlet 31 to flow into the jet generating tube unit 10 on the proximal end of the duct 30 through a proximal end opening 10a of the jet generating tube unit 10.

With such a constitution, the laser irradiation inside the jet generating tube unit 10 is met by the cooling liquid that flows in through the inlet 31, cools first of all the area corresponding with the laser irradiating part 4 that heats up most in the jet generating tube unit 10, flows along the periphery of the jet generating tube unit 10, and flows into the jet generating tube unit 10 through a proximal end opening 10a of the jet generating tube unit 10. Therefore, the outlet 32 or the Y-connector 8 are no longer needed and the complex liquid passage is simplified, making the entire construction extremely simpler.

Figure 15:
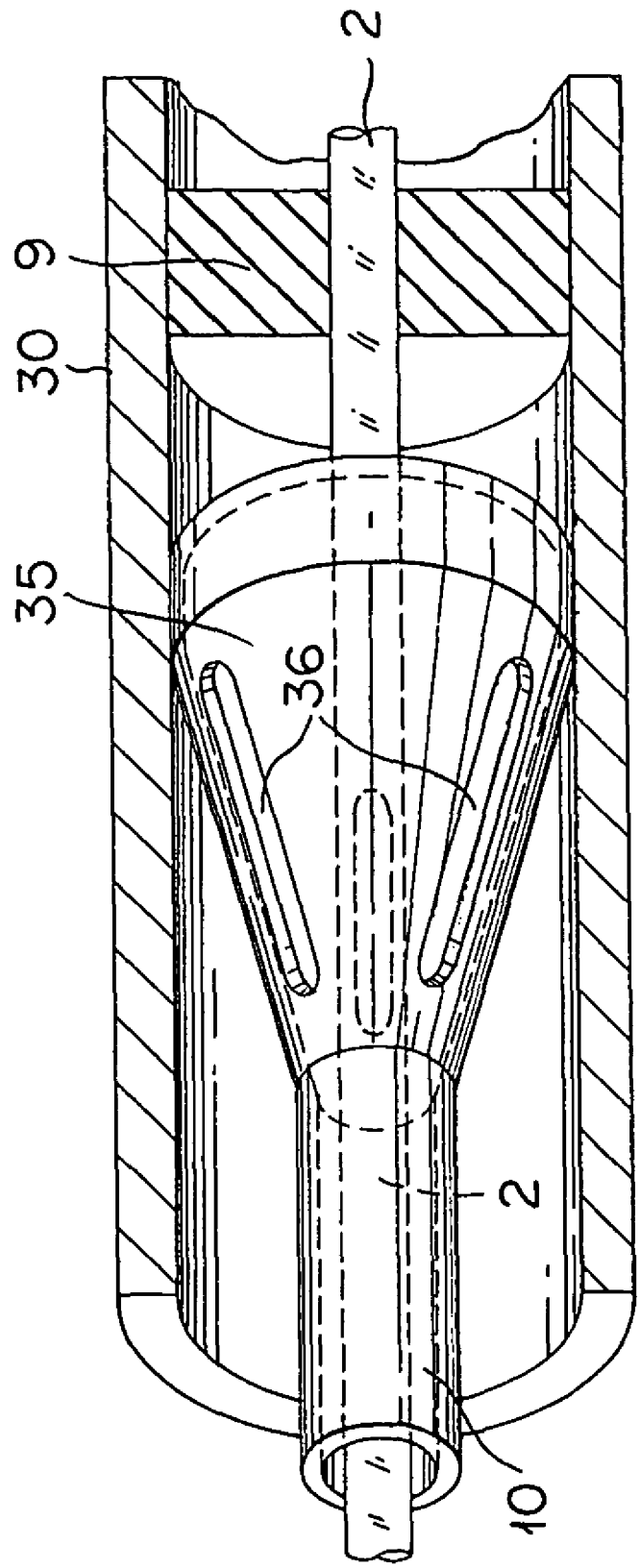
FIG. 15 is an outline perspective drawing showing a key area of FIG. 14.

Although the proximal end of the jet generating tube unit 10 can be simply left opened inside the duct 30, it would construct an unstable free end with nothing to support it, so that it would make it difficult to insert the optical fiber 2. Therefore, it is preferable to have a tube support plate 35 formed in a trumpet-shape at the end of the jet generating tube unit 10 as shown in FIGS. 14 and 15 so that the jet generating tube unit 10 can be supported as the large end of the tube support plate 35 abuts the inner surface of the duct 30. However, it is preferable to have communication openings 36 provided on the tube support plate 35 to allow the cooling liquid to pass through as otherwise the tube support plate 35 may block the liquid W's flow into the jet generating tube unit 10.

As a consequence, the proximal side of the jet generating tube unit 10 is solidly supported inside the duct 30, the cooling liquid flows through the communication openings 36, and the tube support plate 35 is formed in a trumpet-shape, making the insertion of the optical fiber 2 into the jet generating tube unit 10 further easier and improving the workability.

<Third Variation>

Figure 16:
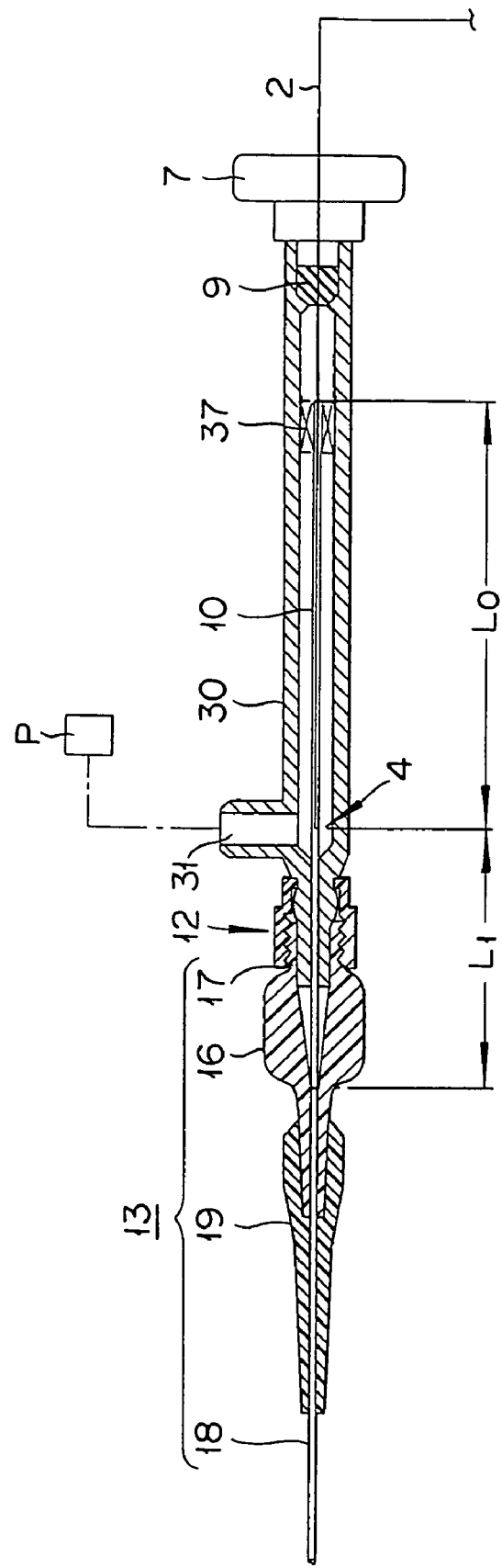
FIG. 16 is an outline cross-sectional drawing of a third variation of the second embodiment.

FIG. 16 shows a third variation of the second embodiment of the invention. Those members common to those in the previously mentioned drawings are labeled in the similar manner to omit the description.

Since the second variation involves the tube support plate 35 of the jet generating tube unit 10, the manufacture of the jet generating tube unit 10 can be slightly more complicated. Consequently, in this variation, a support member 37 is fitted to the proximal side of the duct 30 as a member separate from the jet generating tube unit 10 in order to support the jet generating tube unit 10 generally solidly.

Figure 17:
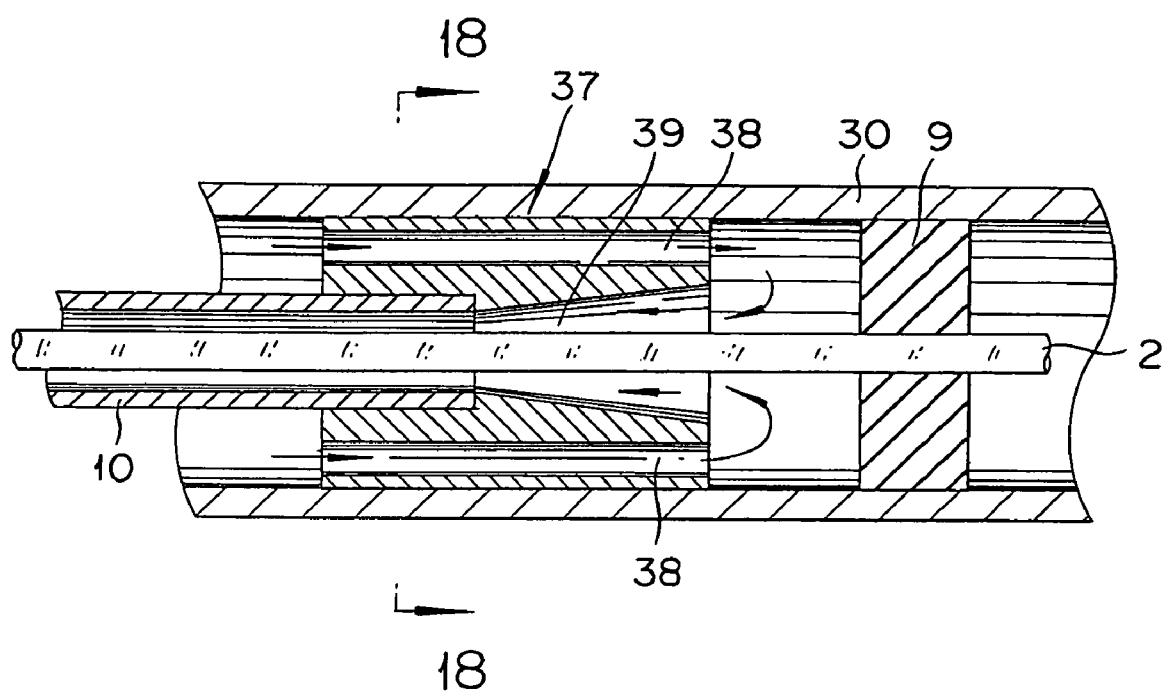
FIG. 17 is an enlarged cross-sectional drawing of the key area of FIG. 16.

Although the support member 37 can have an arbitrary construction so long as it has a liquid transport lumen (communication opening 38) for passage of the cooling liquid and is capable of supporting the jet generating tube unit 10 relative to the inner surface of the duct 30, it is formed in this variation as an axially short tube as shown in FIG. 17 having four communication openings 38 provided in the axial direction to surround an axially centered opening 39 through which the jet generating tube unit 10 is inserted. However, it is preferable to make the axially centered opening 39 trumpet-shaped expanding toward the proximal side as shown in the drawing in order to make the insertion of the optical fiber 2 easier.

With such a constitution, the insertion of the jet generating tube unit 10 is easier even if the optical fiber 2 is to be inserted through the connecting member 7 and the valve body 9 as the proximal side of the jet generating tube unit 10 is supported by the axially centered opening 39 of a supporting member 40 in a fixed manner. Moreover, the cooling liquid flowing in from the inlet 31 can be introduced into the jet generating tube unit 10 through the axially centered opening 39 after making an U-turn through the communication opening 38 of the supporting member 37.

The supporting member 37 can be provided not only at the proximal side of the jet generating tube unit 10 but also in the middle of it.

<Fourth Variation>

Figure 18:
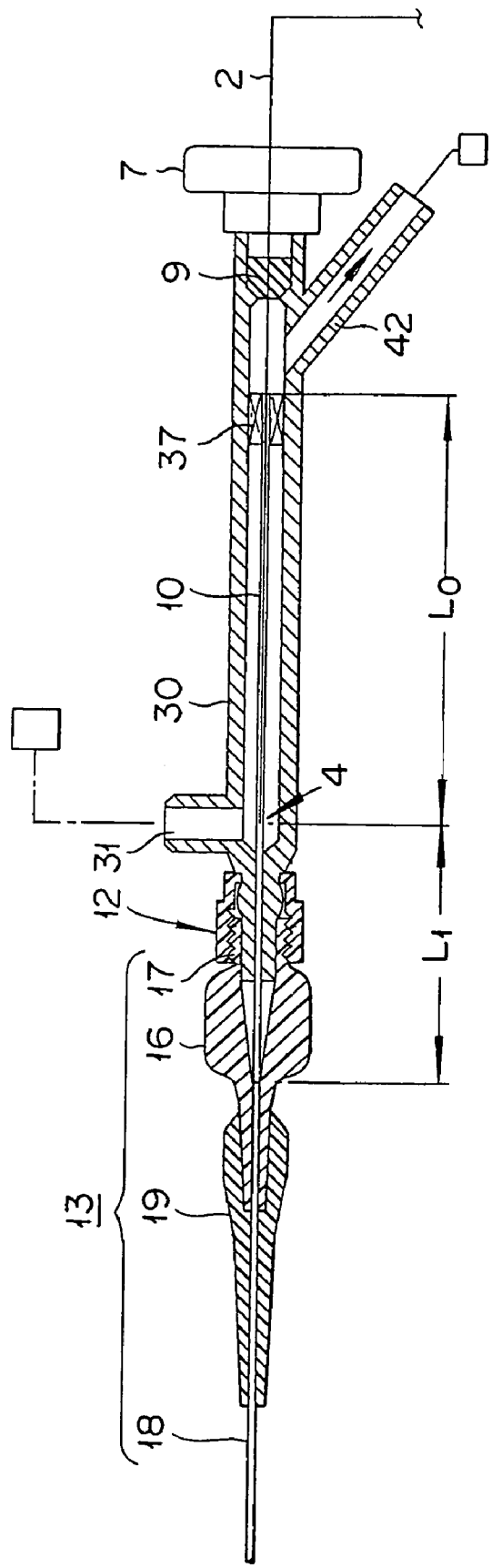
FIG. 18 is a outline cross-sectional drawing of a fourth variation of the second embodiment.

FIG. 18 shows a fourth variation of the second embodiment of the invention. Those members common to those in the previously mentioned drawings are labeled in the similar manner to omit the description.

Since the aforementioned variation uses the duct 30, which is essentially closed on one end, it is impossible to handle a large quantity of the cooling liquid W as the cooling liquid runs through the narrow jet generating tube unit 10. This variation, on the other hand, uses a duct 30 having a side port 42 to discharge the liquid W in order to allow a large volume of the cooling liquid W to flow.

With such a constitution, it is possible to conduct the laser irradiation while allowing a portion of the cooling liquid W entering the duct 30 from the inlet 31 to flow through the jet generating tube unit 10, and the remainder of the cooling liquid W to flow outside through the side port 42, so that it is possible to allow a large volume of the cooling liquid to run along the periphery of the jet generating tube unit 10, thus improving the cooling effect of the jet generating tube unit 10 to allow a long hour of operation. It goes without saying that this construction provides as similar results the previous variation such that it creates a stronger jet stream J and that a device such as a syringe can be connected to the side port 42 to suck out the debris (e.g., the crushed thrombi) together with the cooling water W.

Third Embodiment

Figure 19:
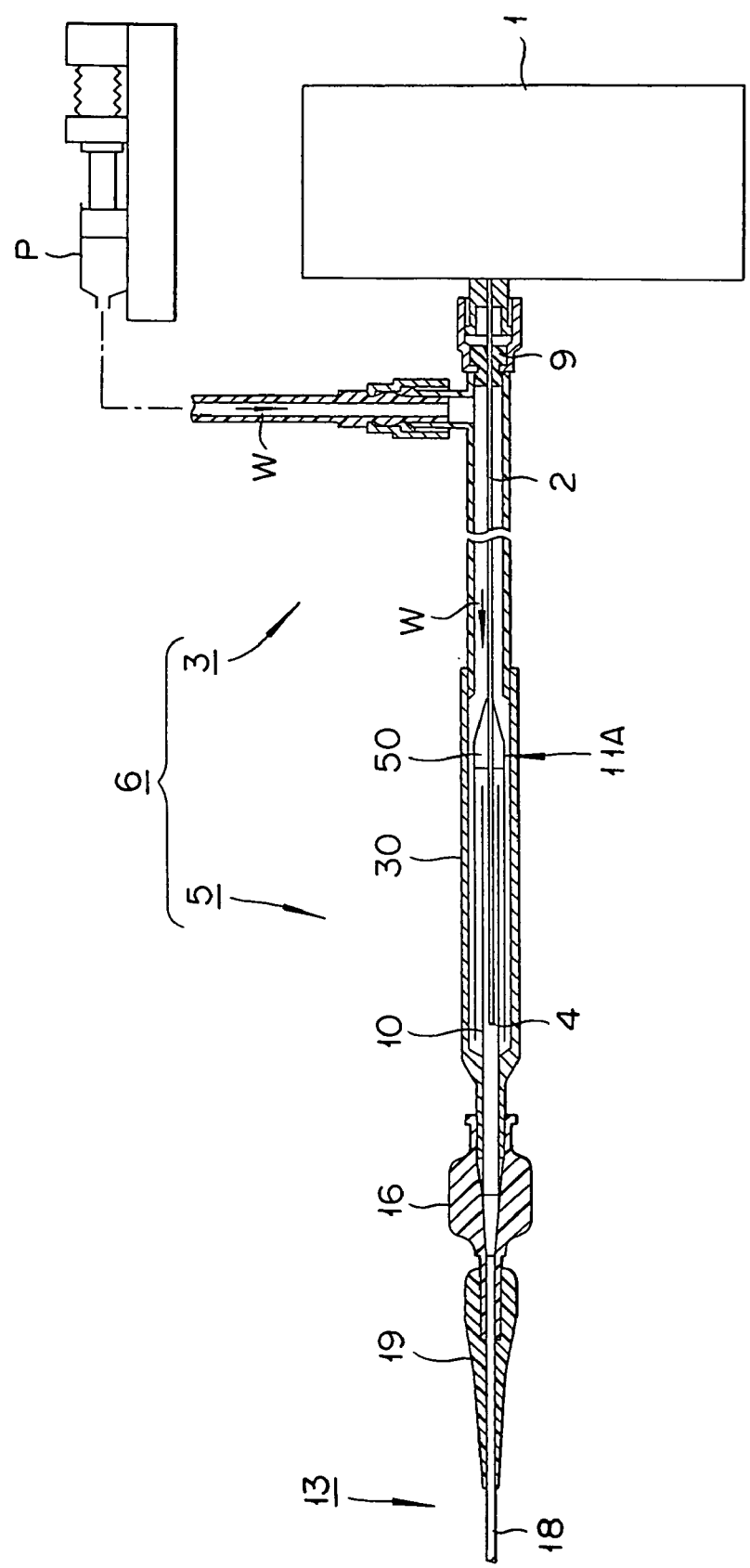
FIG. 19 is an enlarged cross-sectional drawing of a key area of a third embodiment.

FIG. 19 shows a key area of a third embodiment. Those members common to those in the previously mentioned drawings are labeled in the similar manner to omit the description.

The aforementioned jet generating tube unit 10 is constructed in such a way that it prevents laser beams from passing, but the jet generating tube unit 10 of this embodiment is constructed in such a way as to allow laser beams to pass through as the photo/thermal effect of laser beams are shut off by a shut-off means provided separately.

If the jet generating tube unit 10 is transparent (laser beam permeable), the jet generating tube unit 10 tends to absorb little laser beams, thus receiving little photo/thermal effect, so that it is possible to minimize the degeneration and deterioration of the jet generating tube unit 10 and to prolong its life.

While such a jet generating tube unit 10 can be made of: fluorocarbon resins (tetrafluoroethylene-perfluoroalkylvinylether copolymer (PFA), polytetrafluoro-ethylene (PTFE), tetrafluoroethylen hexafluoroprolyne copolymer (FEP)), anhydrous quartz, glass, and sapphire, PTFE increases its whitening effect and increases transmission loss if it is irradiated by laser beams when it is in contact with water, so that it is preferable to use PFA or Lucina (trademark) and Cytop (trademark) of Asahi Glass Co., Ltd. that are entirely include fuluorcarbon polymers including no C—H combinations.

The jet generating tube unit 10 made of those materials preferably does not expand in the radial direction under heavy pressures that occur when the jet stream J is generated, so that the jet stream J can be ejected from the distal end of the tube 18 without essentially losing any of it when the laser beams are applied in pulses.

Although no specific expansion rate is specified so long as the jet stream J can be ejected without essentially losing any of it, the radial expansion rate (the ratio of the difference between the expanded diameter and the pre-expansion diameter to the pre-expansion diameter) should preferably be less than 1%, or more preferably 0.5%, under the condition that one end of the jet generating tube unit 10 or a tube prolonging the jet generating tube unit 10 is sealed liquid tight and the jet generating tube unit 10 or said prolonged tube is filled with a static water of 20 atmospheric pressure, as it would help facilitate ejection of the jet stream J more reliably.

As the shutoff means to shut off the laser beams not to leak to outside of the laser induced liquid jet generating device, it is possibly to use as the liquid W that passes through said duct 30 a liquid having the capability of absorbing laser beams. Another possible format is to have a laser reflection member made of a material similar to those used for the aforementioned light reflection layer or ceramics around the jet generating tube unit 10 at least in the vicinity of the laser irradiating part 4.

Figure 20A:
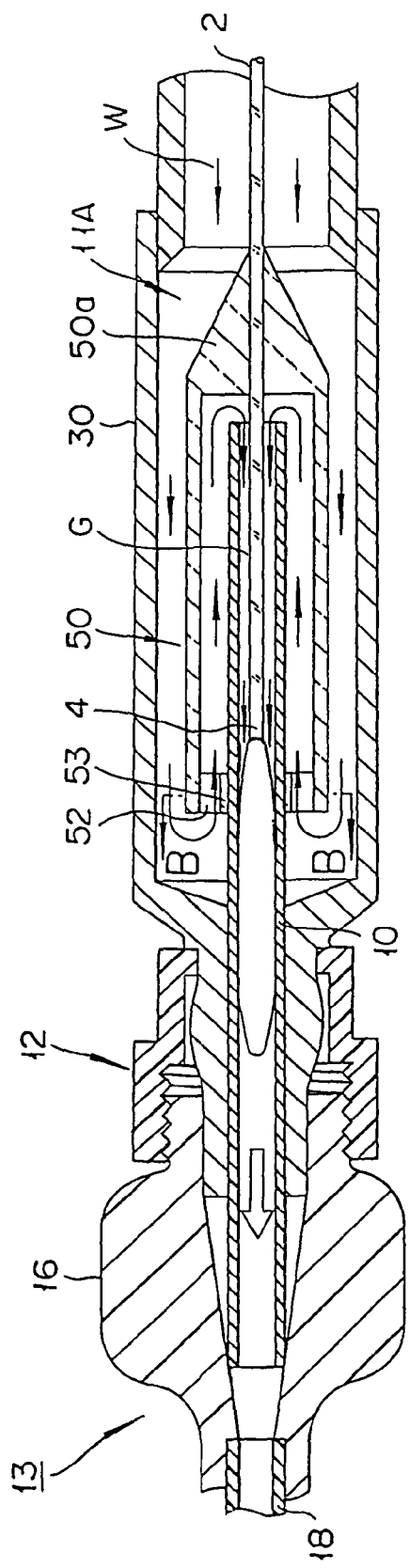
FIG. 20A is an enlarged cross-sectional drawing of a key area showing the jet generating tube unit.

Shut off means 11A of this embodiment is placed inside of the duct 30 as shown in FIG. 20A, and includes a bulkhead member 50 provided on the outside of the jet generating tube unit 10 at least in the vicinity of the laser irradiating part 4 and the liquid W that absorbs laser beams. The bulkhead member 50 is made of plastics such as polyurethane, and its proximal end includes a wall 50a which is formed in a cone shape to reduce the fluid friction, while its distal end is supported by the jet generating tube unit 10.

Figure 20B:
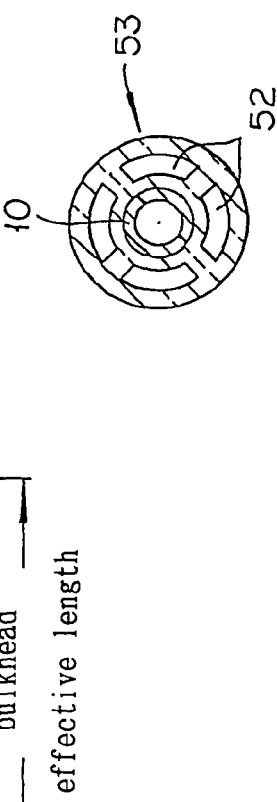
FIG. 20B is a cross-sectional drawing along the line B-B of FIG. 20A.

The distal end of the bulkhead member 50 is provided with a supporting member 53 having a plurality of passages 52 to allow the liquid W to flow in from the outside of the bulkhead member 50 to its inside as shown in FIG. 20B.

By allowing the liquid W to flow in from the distal end of the bulkhead member 50, a fresher supply of the liquid W becomes available to the jet generating tube unit 10 in the vicinity of the laser irradiating part 4 which is more likely to be subjected to the photo/thermal effects. In other words, the liquid W that runs through the duct 30 makes contacts with the jet generating tube unit 10 after traveling from the proximal side to the distal side of the bulkhead member 50, makes a U-turn at the rear end to enter the jet generating tube unit 10, and heads for the laser irradiating part 4.

The liquid W also functions to absorb the laser beams to generally prevent a portion of the laser beams from leaking outside. Consequently, the laser beam shutoff effect can be achieved without having a separate laser beam shutoff means. In other words, the liquid W of this embodiment not only works as a source of generating the jet stream J, i.e., the energy source of the jet stream J that crushes thrombi, it also functions as a laser absorber that absorbs laser beams that pass through the jet generating tube unit 10 so that the laser beam is substancially prevented to leak to outside of the laser induced liquid jet generating device.

Figure 21:
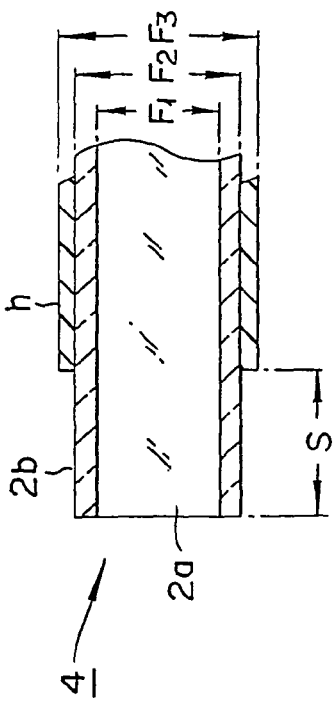
FIG. 21 is an enlarged cross-sectional drawing showing the laser irradiating part of the optical fiber.

The laser irradiating part 4 is formed at the distal end of the optical fiber 2 as shown in FIGS. 20A and 21 by peeling off the coating "h" (polymide resin) on the optical fiber 2 only at the distal end thereof. More specifically, as shown in FIG. 21, it is preferable to peel off a portion with a length "S" of approximately 3 mm, when the diameter F1 of the core 2a is 0.60 mm, the diameter F2 of the cladded area is 0.66 mm, and the diameter F3 of the coating "h" is 0.71 mm.

The laser irradiating part 4 is preferably located at a distance of L1 from the distal end of the jet generating tube unit 10. Such an arrangement causes the jet stream J generated inside the jet generating tube unit 10 to eject powerfully heading toward the ejection port without weakening the jet stream unnecessarily.

Example Experiment

Following results were achieved when an experiment was conducted: The bulkhead member 50 of the experiment had an inner diameter of 3.70 mm, an outer diameter of 4.50 mm, and an effective length of 110 mm and was made of polyurethane. The duct 30 had an inner diameter of 6.00 mm, an outer diameter of 7.00 mm, and a fluid path length of 118 mm and was made of SUS 304 (a stainless steel material according to JIS). The optical fiber 2 was made of anhydrous quartz having an outer diameter of 0.71 mm (core diameter: 0.60 mm) and a length S from the tip of 5 mm. The laser beam was generated by a Ho-YAG laser generator generating 5 W beams with a frequency of 3 Hz. The liquid was supplied at a rate of 360 ml/h.

Several types of tubes were used for the jet generating tube unit 10. The first jet generating tube unit was made of PFA having an inner diameter of 0.85 mm, an outer diameter of 1.85 mm, and an overlap length $L_0$ of 100 mm. The second jet generating tube unit was made of PTFE having an inner diameter of 0.85 mm, an outer diameter of 1.15 mm, and an overlap length $L_0$ of 100 mm. The third jet generating tube unit was made of FEP having an inner diameter of 0.85 mm, an outer diameter of 1.15 mm, and an overlap length $L_0$ of 100 mm. The fourth jet generating tube unit was made of PYREX (registered trademark) glass having an inner diameter of 0.85 mm, an outer diameter of 1.45 mm, and an overlap length $L_0$ of 100 mm. The fifth jet generating tube unit was made of PYREX (registered trademark) glass having an inner diameter of 0.85 mm, an outer diameter of 1.85 mm, and an overlap length $L_0$ of 100 mm.

Although the most ideal kind of materials among various kinds of glass suitable for the jet generating tube unit 10 is anhydrous quartz which provides an extremely small transmission loss for Ho-YAG laser of a wavelength of 2100 mm, it is extremely difficult to produce such a small tube as mentioned above, so that it is preferable to use soda-lime glass and borosilicate glass (for example, PYREX containing approximately 81% of silic acid and approximately 13% of boric acid).

When a jet stream is tested under such a condition, it was able to generate jet streams J for more than 5 minutes for all jet generating tube units 10 tested. Although whitening increased due to the laser irradiation while the PTFE jet generating tube unit 10 is in contact with the liquid W, such a phenomenon was not observed in the FEP and PFA jet generating tube units. It was noted that PFA gave the best result among various resins tested.

A jet stream developed for more than 5 minutes in an experiment using PYREX (registered trademark) glass. It was also noted that experiments using colored glass or glass with high water content ratios may result in absorption of laser beams to cause high temperatures. Although sapphire can be used as well, it is so expensive as anhydrous quartz so that it may not be suitable for medical equipment.

Experiments were also conducted for materials with less laser permeation rates. In other words, jet generating tube units 10 having an inner diameter of 0.85 mm and an outer diameter of 1.15 mm were produced using materials as polystyrene, acrylic, polycarbonate, and urethane resins and were subjected to the similar test. After laser irradiation less than 1 minute, all of them produced holes. Thus, stable jet streams were not available in those cases.

As a indicator of the laser permeability, there is a permeability indicating a percentage ratio of the illuminance data before and after irradiating a plate with a thickness of 1 mm with a laser beam with a wavelength of 2100 mm perpendicularly. The permeability of each material used for producing the jet generating tube unit is shown below. The measurement was conducted at 25° C. using Fild Max-Top Laser Power/Energy Meter available from Coherent Inc.

According to the following table, plate materials with permeability higher than 80% are preferable for producing the jet generating tube unit. As to the wall thickness of the jet generating tube unit is concerned, it is preferable to be less than 2 mm considering the fact that the thicker it is, the more laser beam is absorbed in the jet generating tube unit to make it hotter and also its fitting with the catheter hub.

| Material | Permeation (%) for a wall thickness of 1 mm | Result when used for jet generating tube unit |
| --- | --- | --- |
| Anhydrous quartz | 99.9% or higher | Jet developed for 5 min or more. |
| PFA | 95.1% | Jet developed for 5 min or more. |
| PYREX (trade mark)glass | 94.2% | Jet developed for 5 min or more. |
| Soda-lime glass | 93.4% | Jet developed for 5 min or more. |
| PTFE | 87.0% | Jet developed for 5 min or more. |
| FEP | 82.6% | Jet developed for 5 min or more. |
| Polostyrene | 69.3% | Damaged in 1 min or less. |
| Acrylic resin | 55.9% | Damaged in 1 min or less. |
| Polycarbonate | 47.9% | Damaged in 1 min or less. |
| Urethane resin | 38.3% | Damaged in 1 min or less. |

Fourth Embodiment

Figure 22:
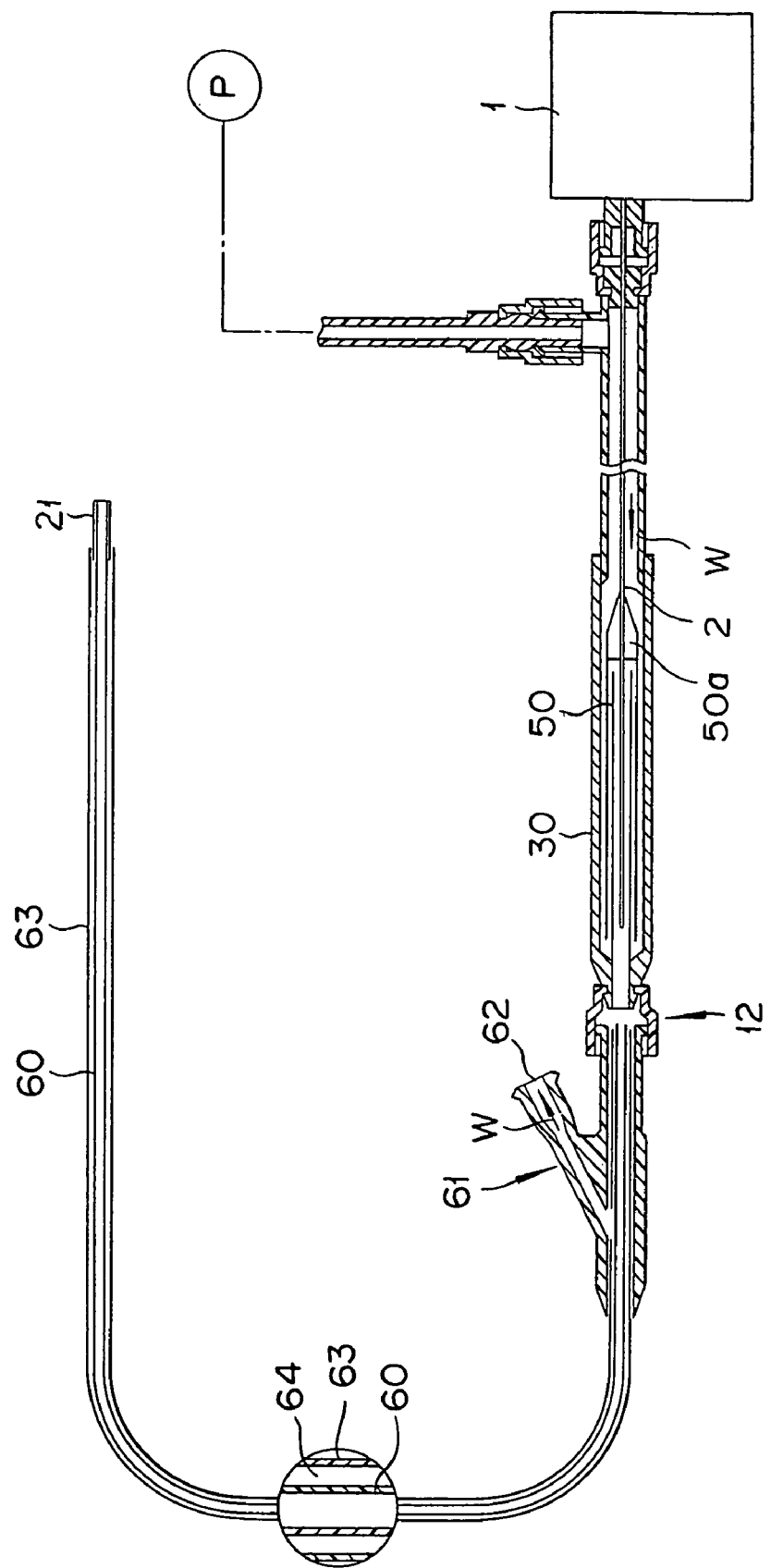
FIG. 22 is an outline cross-sectional drawing of a fourth embodiment.
Figure 23:
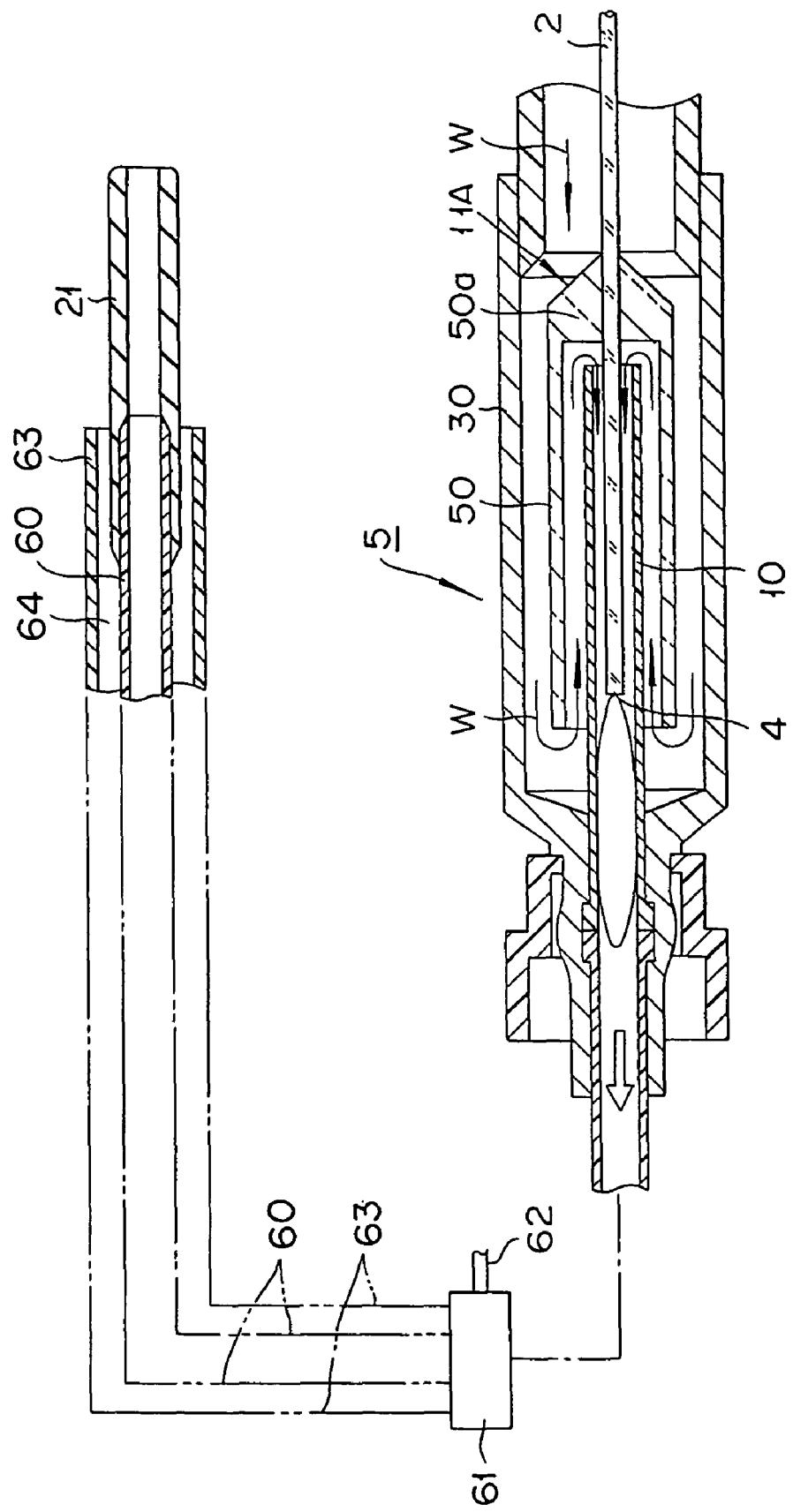
FIG. 23 is an enlarged cross-sectional drawing of the key area of FIG. 22.

FIG. 22 and FIG. 23 show the fourth embodiment of the invention. The members identical to those of the aforementioned embodiments are labeled with similar codes to omit descriptions.

While the aforementioned embodiments used the catheter member 13 at the distal end of the jet generating tube unit 10, i.e., a tube which is relatively soft and deformable, the current embodiment uses a rigid tube 60 which is attached to the tip of the jet generating tube unit 10 which has a sufficient rigidity that allows it to be inserted into an organism, and in which the liquid jet stream J runs through. With such a construction, it is possible for the jet stream J to flow through the rigid tube 60 to allow a more powerful liquid jet stream J to be ejected toward thrombi.

As metallic materials for the rigid tube 60, metals with elasticity or flexibility to withstand deformation inside living organisms, such as superelastic alloys and Rubber Metal (trade mark registered by Toyota Central Laboratory) are preferable. Superelastic alloys are also generally known as shape-memory alloys and show superelasticity at least in the vicinity of the body temperature (37° C.). Superelasticity metals such as TiNi alloy containing 49-53 atomic % of Ni, Cu—Zn alloy containing 38.5-41.5 weight % of Zn, Cu—Zn—X alloy (X=Be, Si, Sn, Al, Ga) containing 1-10 weight % of X, and Ni—Al alloy containing 36-38 atomic % of Al are preferable for the aforementioned purpose. TiNi alloy is most preferable among them. While polyimide, polyetherimide, polycarbonate, and polyester with a Shore D Hardness Hs of 70 or higher are preferable for the same purpose, but it is also preferable to enhance their rigidity by containing braids. It is also preferable, in this embodiment as well, to provide a protective member 21 consisting of a soft material on the distal side of the rigid tube 60 in order to mitigate damages on blood vessel walls.

Moreover, as shown in FIG. 22 and FIG. 23, it is possible to conduct a treatment while sucking (see the arrow in FIG. 22) thrombi through a suction port 62 of a branching hub 61 of a guide catheter 63, by connecting the guide catheter 63 having the suction port 62 to the duct 30 via the catheter mounting unit 12 and the branching hub 61. In this case, it is necessary to have a clearance 64 allowing suction between the guide catheter 63 and the rigid tube 60 without uniting them in a liquid-tight manner.

Fifth Embodiment

Figure 24:
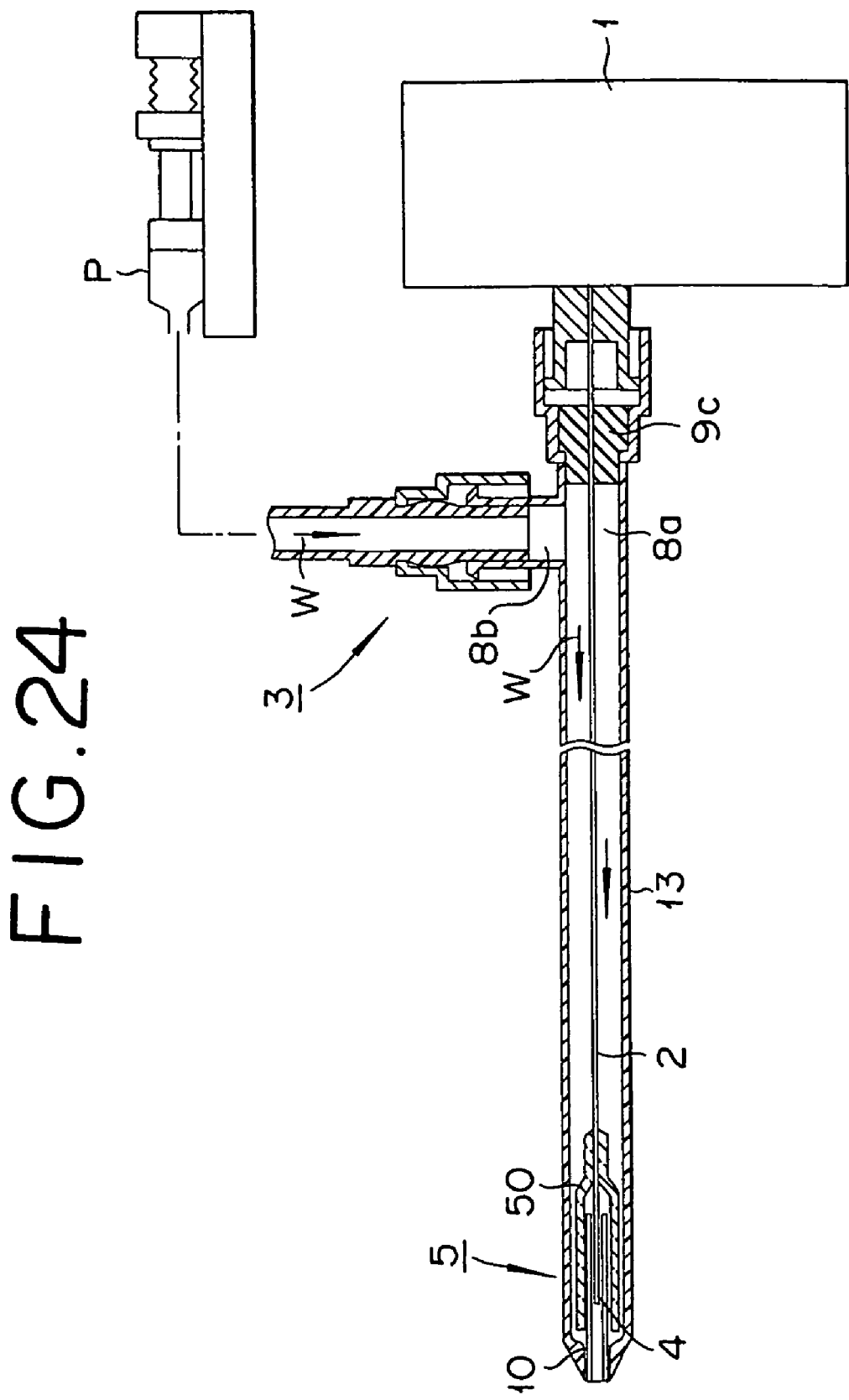
FIG. 24 is an outline cross-sectional drawing of a fifth embodiment.
Figure 25:
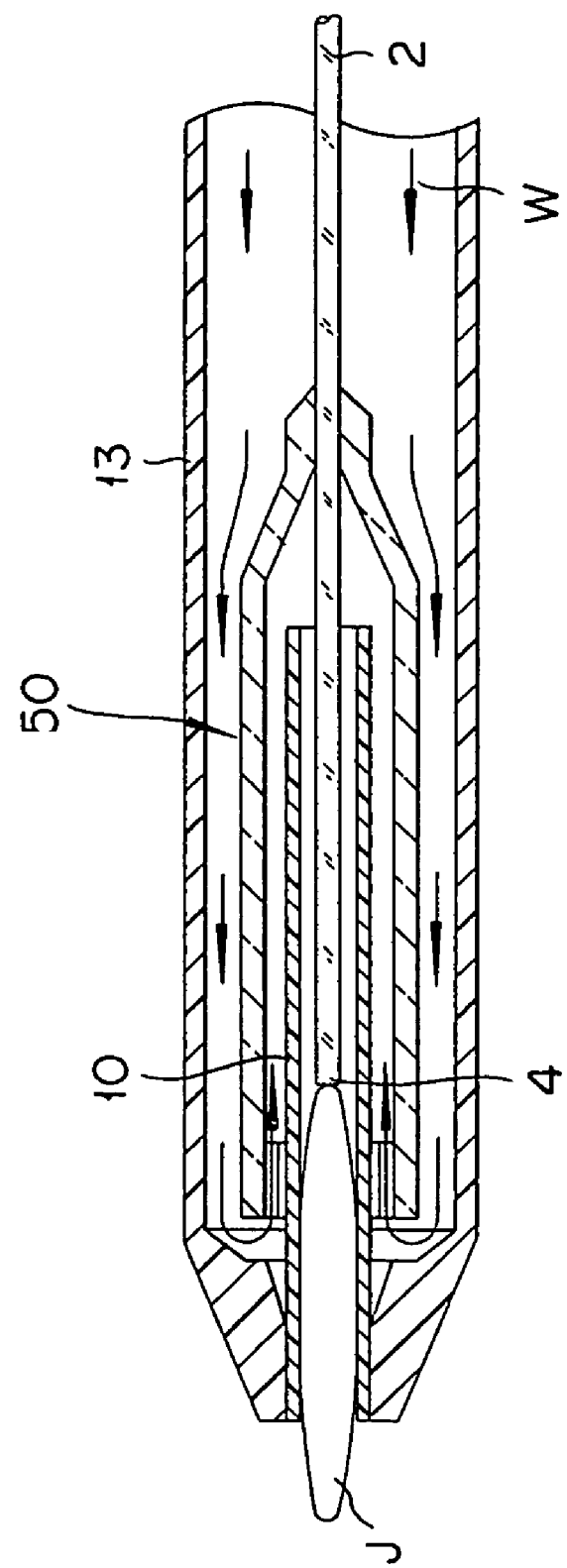
FIG. 25 is an enlarged cross-sectional drawing of a key area showing the jet generating tube unit of said embodiment.

FIG. 24 shows the fifth embodiment. FIG. 25 is an enlarged cross-sectional drawing of a key area showing the jet generating tube unit of said embodiment. The members identical to those of the aforementioned embodiments are labeled with similar reference numbers to omit descriptions.

While the operating unit 5 having the jet generating tube unit 10 is provided on the proximal side of the catheter member 13 for the convenience of the operator in the aforementioned embodiments, it is placed in the lumen of the catheter member 13 in the present embodiment. With such a configuration, the jet stream J can be generated in the vicinity of the affected area, so that it is possible to generate a strong jet stream J with the same laser output, or the same level of jet stream J as the aforementioned embodiments with a weaker output.

Although it is necessary to adjust the length of the jet generating tube unit 10 and the clearance between it and the optical fiber 2 in order to optimize the output because a certain pressure loss is inevitable due to the fact that the jet stream J flows through the length of the catheter member 13 in the aforementioned embodiments, there is no such need in the present embodiment and a greater degree of freedom is available for the length of the jet generating tube unit 10 and the clearance between it and the optical fiber 2.

What is claimed is:

1. A laser induced liquid jet generating device comprising:
   a main body possessing a lumen therein, wherein the main body comprises:
   an connector disposed to communicate with the lumen of said main body, and intended to fit an optical fiber furnished with a laser irradiating part for allowing introduction of a laser beam from a laser oscillator into the lumen,
   a liquid injecting member for injecting into the lumen of said main body a liquid capable of absorbing said laser beam,
   a jet generating tube unit configured to combine radiation emitted from the laser irradiating part of the optical fiber with the liquid ejected out of the liquid injecting member to generate jet streams of said liquid;
   a catheter mounting unit mounted integrally or in a removable manner on a catheter member into which said jet stream is introduced; and
   a heat transfer inhibition means for inhibiting thermal effect due to laser beams emitted by said laser irradiating part from being transferred outside of said jet generating tube unit, wherein said heat transfer inhibition means is configured to surround the laser irradiating part of said optical fiber.

2. A laser induced liquid jet generating device claimed in claim 1 wherein a gap between said jet generating tube unit and said laser irradiating part and a distance said optical fiber overlaps with said jet generating tube unit are determined in such a manner that the flow direction of said jet stream is restricted.

3. A laser induced liquid jet generating device claimed in claim 1 wherein a distal end of the jet generating tube unit is concentric with an inlet of the catheter member.

4. A laser induced liquid jet generating device claimed in claim 1 wherein a distal end of the jet generating tube unit is connected substantially liquid-tight with an inlet of the catheter member.

5. A laser induced liquid jet generating device claimed in claim 1 wherein said optical fiber is contained in such a way that said laser irradiating part keeps a specified distance from said jet generating tube unit's distal end.

6. A laser induced liquid jet generating device claimed in claim 1 wherein said main body comprise affixing means for affixing a distal end of the optical fiber related to said jet generating tube unit.

7. A laser induced liquid jet generating device claimed in claim 1 wherein said heat transfer inhibition means comprise a thermal insulator covering an outer periphery of said jet generating tube unit at least at an axial location corresponding to said laser irradiating part.

8. A laser induced liquid jet generating device claimed in claim 1 wherein said heat transfer inhibition means is comprising a duct laid out to cause a cooling liquid to flow around said jet generating tube unit.

9. A laser induced liquid jet generating device claimed in claim 8 wherein said duct is provided at a location corresponding to said laser irradiating part or in front thereof, has an inlet through which said cooling liquid flows in and an outlet through which said cooling liquid flows out, so that said cooling liquid flowing in through said inlet flows along said jet generating tube unit's periphery and flows out through said outlet.

10. A laser induced liquid jet generating device claimed in claim 8 wherein said duct has a guide tube that guides said cooling liquid, which is flowing out of an outlet, into said jet generating tube unit.

11. A laser induced liquid jet generating device claimed in claim 8 wherein said duct has an inlet at a location that corresponds to said laser irradiating part so as to causes said liquid to flow in from a proximal side of said jet generating tube unit.

12. A laser induced liquid jet generating device claimed in claim 8 wherein said duct has an inlet and an outlet at a location that corresponds to a distal end of said jet generating tube unit.

13. A laser induced liquid jet generating device claimed in claim 8 wherein said duct has a support member in the inside in order to support said jet generating tube unit and said support member is provided with communication openings in order to allow said cooling liquid to pass through.

14. A laser induced liquid jet generating device claimed in claim 8 wherein said jet generating tube unit has a tube support plate for supporting said jet generating tube unit on its proximal side abutting the inside of said duct and said tube support plate has communication openings in order to allow said cooling liquid to pass through.

15. A laser induced liquid jet generating device claimed in claim 1 wherein an inner wall at least in the vicinity of distal end of said jet generating tube unit contains a material that reflects laser beam.

* * * * *